US011754568B2

United States Patent
Tsuji

(10) Patent No.: US 11,754,568 B2
(45) Date of Patent: Sep. 12, 2023

(54) REAGENT SELECTION SUPPORT APPARATUS, CELL ANALYSIS SYSTEM, REAGENT SELECTION SUPPORT METHOD, AND STORAGE MEDIUM STORING COMPUTER PROGRAM

(71) Applicant: SYSMEX CORPORATION, Kobe (JP)

(72) Inventor: Tomohiro Tsuji, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 1031 days.

(21) Appl. No.: 16/420,443

(22) Filed: May 23, 2019

(65) Prior Publication Data

US 2019/0360910 A1    Nov. 28, 2019

(30) Foreign Application Priority Data

May 25, 2018    (JP) .................................. 2018-100268

(51) Int. Cl.
*G01N 33/58* (2006.01)
*G01N 15/14* (2006.01)
(Continued)

(52) U.S. Cl.
CPC ....... *G01N 33/582* (2013.01); *G01N 15/1404* (2013.01); *G01N 15/1429* (2013.01);
(Continued)

(58) Field of Classification Search
CPC ........... G01N 15/1404; G01N 15/1429; G01N 33/582; G01N 35/00584; G01N 33/54386; G01N 33/533
See application file for complete search history.

(56) References Cited

U.S. PATENT DOCUMENTS

| 8,415,161 B2 | 4/2013 | Yan et al. |
| 2013/0224851 A1* | 8/2013 | Ljungmann ........... B04B 5/0421 |
| | | 435/308.1 |
| 2018/0285754 A1* | 10/2018 | Yao ........................ G06N 5/045 |

FOREIGN PATENT DOCUMENTS

| EP | 1431745 A1 | 6/2004 |
| EP | 2187199 A1 | 5/2010 |

(Continued)

OTHER PUBLICATIONS

Communication pursuant to Article 94(3) EPC dated Jun. 22, 2020 in a counterpart European patent application No. 19174340.0.

(Continued)

*Primary Examiner* — Gailene Gabel
(74) *Attorney, Agent, or Firm* — Crowell & Moring LLP

(57) ABSTRACT

A reagent selection support apparatus for supporting selection of a reagent used for cell measurement is provided. The apparatus includes a processing unit configured to acquire order information including a first measurement item and a second measurement item different from the first measurement item, and determine a combination of a first fluorescence reagent used to measure a first target molecule corresponding to the first measurement item and a second fluorescence reagent used to measure a second target molecule corresponding to the second measurement item, based on information on a property of the first target molecule and a property of a first fluorescent stain contained in the first fluorescent reagent, and information on a property the second target molecule and a property of a second fluorescent stain contained in the second fluorescent reagent; and an output unit configured to output the determined combination of the first fluorescence reagent and the second fluorescence reagent.

17 Claims, 16 Drawing Sheets

(51) Int. Cl.
  *G01N 35/00* (2006.01)
  *G01N 33/543* (2006.01)
  *G01N 33/533* (2006.01)
  *G06F 16/903* (2019.01)

(52) U.S. Cl.
  CPC ..... *G01N 33/533* (2013.01); *G01N 33/54386* (2013.01); *G01N 35/00584* (2013.01); *G06F 16/903* (2019.01)

(56) References Cited

FOREIGN PATENT DOCUMENTS

| EP | 2426481 A1 | 3/2012 |
| JP | 2011-085587 A | 4/2011 |
| JP | 2016-517000 A | 6/2016 |
| WO | 2014/144826 A1 | 9/2014 |
| WO | 2017/011549 A1 | 1/2017 |

OTHER PUBLICATIONS

Extended European search report dated Oct. 14, 2019 in a counterpart European patent application No. 19174340.0.
Communication pursuant to Article 94(3) EPC dated Dec. 11, 2020 in a counterpart European patent application No. 19174340.0.
Japanese Office Action dated Mar. 8, 2022 in Japanese patent application No. 2018-100268.
Holden Maecker et al., "Selecting reagents for multicolor flow cytometry with BD™ LSR II and BD FACSCanto™ systems", Nature Methods, Dec. 2008, pp. 1-2, an6-an7, vol. 5, Nature Publishing Group.
Japanese Office Action with English Machine Translation, dated Nov. 8, 2022, pp. 1-8, Issued in Japanese patent application No. 2018-100268, Japan Patent Office, Tokyo, Japan.

\* cited by examiner

FIG. 6

| Cell type | Target molecule | Number of molecules/cell |
|---|---|---|
| T-cell | TCR | 100,000 |
| | CD2 | 55,000 |
| | CD3 | 124,000 |
| | CD5 | 90,000 |
| | CD7 | 20,000 |
| | CD45 | 200,000 |
| CD4 positive T-cell | CD4 | 100,000 |
| | CD28 | 20,000 |
| | CCR5 | 4,000 |
| | | 24,000 |
| CD8 positive T-cell | CD8 | 90,000 |
| | CD28 | 15,000 |
| B cell | CD19 | 18,000 |
| | CD20 | 109,000 |
| | CD21 | 210,000 |
| | CD22 | 14,000 |
| | HLA-DR | 85,000 |
| | CD11a | 10,000 |
| | CD40 | 2,000 |
| | CD86 | 16,000 |
| | CD80 | 2,000 |
| Dendritic cell | CD11a | 27,000 |
| | CD40 | 17,000 |
| | CD80 | 132,000 |
| | CD86 | 208,000 |
| monocyte | CD14 | 110,000 |
| | CD32 | 21,000 |
| | CD64 | 13,000 |
| Neutrophil | CD14 | 3,500 |
| | CD16 | 225,000 |
| NK cell | CD56 | 10,000 |
| Blood cell | Gly-A | 340,000 |
| Basophil | CD23 | 15,000 |

FIG. 7

| Fluorescent reagent | A | | B | |
|---|---|---|---|---|
| Measurement device | L | | L | |
| Antibody | CD4 antibody | | CD4 antibody | |
| Fluorescent stain | | Stain Index | | Stain Index |
| | PE-Cy5 | 353 | PE | 305 |
| | PE | 302 | APC | 263 |
| | APC | 278 | PE-Cy5 | 198 |
| | AF647 | 214 | AF647 | 184 |
| | PE-Cy7 | 139 | PE-Cy7 | 122 |
| | PerCP-Cy5.5 | 107 | PerCP-Cy5.5 | 99 |
| | SV450 | 85 | AF488 | 68 |
| | Pacific Blue | 80 | SV450 | 65 |
| | AF488 | 73 | AF700 | 64 |
| | AF700 | 61 | Pacific Blue | 63 |
| | FITC | 56 | FITC | 43 |
| | APC-Cy7 | 37 | AmCyan | 37 |
| | PrepCP | 37 | APC-Cy7 | 36 |
| | AmCyan | 25 | PrepCP | 30 |
| | APC-H7 | 24 | SV500 | 27 |
| | | | APC-H7 | 25 |

FIG. 10

| 1st candidate | (Running cost : ¥100<br>Shortest expiration date: July 1, 2018<br>Residual reagent: No) | |
|---|---|---|
| Measurement item | Fluorescent stain | Fluorescent reagent name |
| CD4 | PerCP | Antibody reagent α |
| CD28 | PE | Antibody reagent β |

| 2nd candidate | (Running cost : ¥150<br>Shortest expiration date: July 1, 2018<br>Residual reagent: Yes) | |
|---|---|---|
| Measurement item | Fluorescent stain | Fluorescent reagent name |
| CD4 | AmCyan | Antibody reagent γ |
| CD28 | APC | Antibody reagent δ |

FIG. 11

| Priority order | Reagent expiration date<br>Residual reagent<br>User specified fluorescent<br>stain |
|---|---|

- PE
- APC
- PE-Cy5
- AF647
- PE-Cy7
- PerCP-Cy5.5
- AF488
- SV450
- AF700
- Pacific Blue
- FITC
- AmCyan
- APC-Cy7
- PrepCP
- SV500
- APC-H7

REAGENT SELECTION SUPPORT APPARATUS, CELL ANALYSIS SYSTEM, REAGENT SELECTION SUPPORT METHOD, AND STORAGE MEDIUM STORING COMPUTER PROGRAM

RELATED APPLICATIONS

This application claims priority from prior Japanese Patent Application Publication No. 2018-100268, filed on May 25, 2018, entitled "Reagent Selection Support Apparatus, Cell Analysis System, Reagent Selection Support Method, and Storage Medium Storing Computer Program", the entire contents of which are incorporated herein by reference.

BACKGROUND OF THE INVENTION

1. Field of the Invention

The present disclosure relates to a reagent selection support apparatus, a cell analysis system, a reagent selection support method, and a storage medium storing a computer program.

2. Description of the Related Art

Flow cytometry, as disclosed in, for example, Japanese Patent Application Publication No. 2011-085587, can detect various antigens present on the cell surface or in cells in combination with fluorescence immunostaining, and is particularly useful for analysis of cells.

In order to measure more antigens efficiently, a multicolor flow cytometry for detecting multiple antigens in one assay is generally performed.

In recent years, with the elucidation of the entire sequence of the human genome and advances in the technology for producing transgenic animals, it has become possible to analyze the association with diseases even with molecules whose expression level is low in cells. In recent years, the number of fluorescent stains that can be detected at one time has also increased due to an increase in the number of light sources mounted on flow cytometers and progress in optical systems used in detection such as dichroic mirrors for dispersing light and the like. In the analysis of various molecules present in cells, flow cytometry has become a useful tool that can analyze multiple antigens in a single assay.

Flow cytometry is a technology that is a major contributor to disease diagnosis, disease stage determination, and treatment decisions. The spread of flow cytometry has made it possible to accurately identifying cell lineage of tumor cells, and the diagnosis of hematopoietic tumors, which was previously performed based on cell morphological observation, enzyme staining, and immunostaining, has shifted to diagnosis often based on cell surface marker profiling. Analysis of multiple types of antigens is required for diagnosis of diseases, and it is usual that analysis of multiple types of antigens is requested in one test order as a measurement item by flow cytometry.

For example, it is necessary to detect 10 to 30 surface markers per sample just to identify whether it is a B cell tumor. In order to detect all targeted surface markers, multicolor flow cytometry using several to 10 kinds of detection antibodies, in which the labeled fluorescent stain is different for each antigen of a single assay per sample, must be performed multiple times while changing the detection antibody.

However, in order to detect multiple types of antigens in one assay, it is necessary to select antigens according to the cell type to be detected as well as to know in advance that no cross reactivity of a detection antibody occurs between its target antigen and another antigen that is simultaneously detected in the assay. It also is necessary to select a combination of detection antibodies that can be used for the assay from the detection antibodies on hand at the time of examination.

Under these circumstances, flow cytometry is currently performed exclusively by a specialist who has knowledge of the property of the detection antibody and the flow cytometer, and it is a fact that a person with such specialized knowledge exclusively select the detection antibody reagent according to the measurement item ordered.

SUMMARY OF THE INVENTION

In addition to the above, when a plurality of different target molecules (such as antigens) are detected using different fluorescent stains in one assay, as in multicolor flow cytometry, for example, the abundance in one cell may differ for each target molecule. As for the fluorescent stain, a difference of 10 times or more in the fluorescence intensity also is recognized depending on the stain. Therefore, when a fluorescent stain with high fluorescence intensity is used to detect a large amount of a target molecule, there is a problem that a small amount of a target molecule to be simultaneously assayed may not be detected. For this reason, it is necessary to decide before the measurement which combination of fluorescent stains to use to perform one assay. However, at present, the combination of the fluorescent stains is determined based on the experience of the examiner.

There is a need at hospital laboratories to "provide stable examination results on demand, promptly and always." However, examinations using flow cytometry are becoming more complicated year by year, and it is difficult for persons other than a specialized examiner to decide what combination of fluorescent stains to use when in a single assay. For this reason, as the technology of flow cytometry advances, it deviates significantly from the above-mentioned needs in the field of hospital examinations.

Although the method of Japanese Patent Application Publication No. 2011-085587 is a method aiming to simplify the setup of devices such as flow cytometers, it is a method based on the premise of an examiner having a certain level of professional knowledge, and is not a user-friendly for neophytes. The method of Japanese Patent Application Publication No. 2011-085587 does not satisfy the above-described needs which are required for the examination lab of a hospital.

In the case of multicolor flow cytometry, if a second fluorescence is extremely low compared to a first fluorescence, the fluorescence resulting from the strong first fluorescence leaks into the detector that detects the second fluorescence, which raises the problem of, for example, adverse effects caused by the leaked light on the detection of the weak second fluorescence.

The present disclosure supports determining a combination of a plurality of fluorescent reagents independently of an examiner's skill level.

One embodiment of the present disclosure relates to a reagent selection support apparatus (100, 100B) that supports selection of a reagent used for cell measurement. The reagent selection support apparatus includes a processing unit (10A, 10B) configured to acquire order information including a first measurement item and a second measurement item different from the first measurement item, and determine a combination of a first fluorescence reagent used to measure a first target molecule corresponding to the first measurement item and a second fluorescence reagent used to measure a second target molecule corresponding to the second measurement item, based on information on a property of the first target molecule and a property of a first fluorescent stain contained in the first fluorescent reagent, and information on a property the second target molecule and a property of a second fluorescent stain contained in the second fluorescent reagent; and an output unit configured to output the determined combination of the first fluorescence reagent and the second fluorescence reagent. According to this embodiment, the combination of a plurality of fluorescent reagents to be used in one assay can be determined regardless of the examiner's skill in the cell analysis technology.

Preferably, the antigen includes at least one of nucleic acid, protein, sugar chain, lipid, glycoprotein, glycolipid, lipoprotein, and ion present in the cell. In this way, the measurement with nucleic acid or antigen as the target molecule is a test order with a high test order frequency according to the measurement item, and cell analysis with a high test order frequency can be supported.

Preferably, the property of the fluorescent stain is a value indicating fluorescence intensity, and the property of the target cell is the amount of molecules present in the cell. More specifically, the property of the fluorescent stain is a staining index, and the processing unit (10A, 10B) calculates information related to brightness of the first fluorescent stain based on the staining index of the first fluorescent stain and a value reflecting the amount of target molecules corresponding to the first measurement item present in the measurement target cell, calculates information related to the brightness by the second fluorescent stain based on the staining index of the second fluorescent stain and a value reflecting the amount of the second target molecule corresponding to the second measurement item present in the measurement target cell, and determines the combination based on information related to the brightness by the first fluorescent stain and information related to the brightness by the second fluorescent stain. Preferably, the value reflecting the amount of the first target molecule and the value reflecting the amount of the second target molecule are the absolute number of molecules of each target molecule present in the measurement target cell or the relative number of molecules of each target molecule.

The reagent selection support apparatus (100, 100B) includes a storage unit configured to store the staining index of the first fluorescent stain and the staining index of the second fluorescent stain. The reagent selection support apparatus (100, 100B) includes a storage unit configured to store a value reflecting the amount of the first target molecule corresponding to the first measurement item present in the measurement target cell, and a value reflecting the amount of the second target molecule corresponding to the second measurement item present in the measurement target cell. With such a configuration, it is possible to support the selection of the fluorescent reagent even if the reagent selection support apparatus (100, 100B) is not always connected to a network.

The processing unit (10A, 10B) determines the combination of the first fluorescent reagent and the second fluorescent reagent based on the information related to the brightness of the first fluorescent stain and the dispersion of the information on the brightness of the second fluorescent stain. With such a configuration, it is possible to determine a combination of fluorescent reagents having as little difference as possible between the fluorescent reagents regarding the fluorescence signals emitted from one cell.

Preferably, the reagent includes an antibody labeled with a fluorescent stain. Preferably, an antibody for detecting one type of antigen is included. According to the present disclosure, a plurality of antigens can be simultaneously detected by a combination of appropriate fluorescent stains without using a cocktail antibody.

The reagent contains multiple types of antibodies. With such a configuration, reagents can be selected even when using a cocktail antibody.

Preferably, the processing unit (10A, 10B) determines a plurality of combinations of the first fluorescent reagent and the second fluorescent reagent, and the output unit (17) outputs the combination with a priority based on the remaining amount of the reagent contained in the fluorescent reagent. In this way it is possible to select the reagent in consideration of the remaining amount of the reagent.

The processing unit (10A, 10B) determines a plurality of combinations of the first fluorescent reagent and the second fluorescent reagent, and the output unit (17) outputs the combination with a priority based on the expiration date of the fluorescent reagent. In this way, it is possible to select the reagent in consideration of the expiration date of the reagent.

The processing unit (10A, 10B) determines a plurality of combinations of the first fluorescent reagent and the second fluorescent reagent, and the output unit (17) outputs the combination with a priority based on the cost of the fluorescent reagent. In this way, it is possible to select the reagent in consideration of the running cost.

The processing unit (10A, 10B) determines a plurality of combinations of the first fluorescent reagent and the second fluorescent reagent, and the output unit (17) outputs the combination with a priority based on the setting designated by the user. In this way, it is possible to select the reagent in consideration of the priority of the user.

The reagent selection support apparatus (100B) includes a communication unit (151) that receives information on the property of the fluorescent stain. In this way, the reagent selection support apparatus (100B) can always determine the combination of fluorescent reagents based on new information.

The reagent selection support apparatus (100B) includes a communication unit that receives information on the property of the target molecule present in the measurement target cell. In this way, the reagent selection support apparatus (100B) can always determine the combination of fluorescent reagents based on new information.

An embodiment of the present disclosure relates to a cell analysis system (1000, 4000) including a reagent selection support apparatus (100, 100B), and a cell analysis apparatus (200) having a measurement unit (23) that measures cells by flow cytometry. Preferably, the measurement unit (23) measures fluorescence generated from the first fluorescent stain and fluorescence generated from the second fluorescent stain obtained from the same cell. In this way, even inexperienced examiners can perform the examinations in the complicated flow cytometry examination.

One embodiment of the present disclosure relates to a reagent selection support method used in cell measurement including acquiring order information including a first measurement item and a second measurement item different from the first measurement item: determining a combination of a first fluorescence reagent used to measure a first target molecule corresponding to the first measurement item and a second fluorescence reagent used to measure a second target molecule corresponding to the second measurement item based on information on a property of the first target molecule and a property of a first fluorescent stain contained in the first fluorescent reagent, and information on a property the second target molecule and a property of a second fluorescent stain contained in the second fluorescent reagent; and outputting the determined combination of the first fluorescent reagent and the second fluorescent reagent.

One embodiment of the present disclosure relates to a non-transitory storage medium storing a computer program executable by a computer to acquire order information including a first measurement item and a second measurement item different from the first measurement item: determine a combination of a first fluorescence reagent used to measure a first target molecule corresponding to the first measurement item and a second fluorescence reagent used to measure a second target molecule corresponding to the second measurement item based on information on a property of the first target molecule and a property of a first fluorescent stain contained in the first fluorescent reagent, and information on a property the second target molecule and a property of a second fluorescent stain contained in the second fluorescent reagent; and output the determined combination of the first fluorescent reagent and the second fluorescent reagent.

According to the present disclosure, it is possible to select an appropriate combination of fluorescent reagents in accordance with an examination order even if the examiner does not have specialized knowledge.

BRIEF DESCRIPTION OF THE DRAWINGS

FIG. 6 is an example of a list table showing information of target molecules;

FIG. 7 is an example of a list table showing information of fluorescent stains;

FIG. 10 is an example of a fluorescent reagent candidate;

FIG. 11 is an example of a priority selection list;

DETAILED DESCRIPTION OF THE PREFERRED EMBODIMENTS

Figures 1A, 1B:
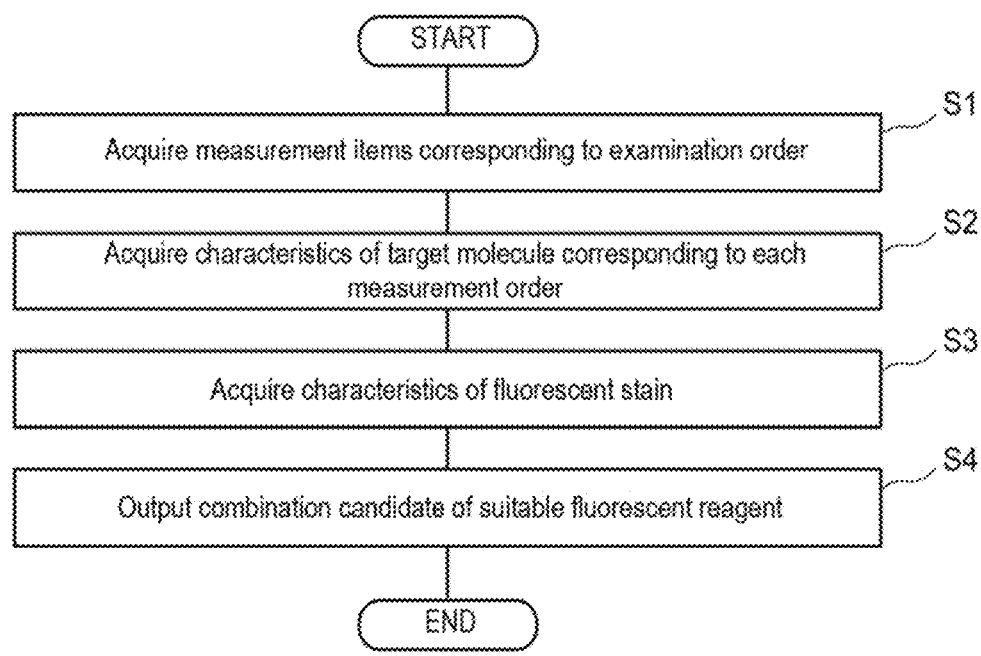
FIG. 1A and FIG. 1B show an overview of the present disclosure.

Hereinafter, embodiments of the present invention will be described in detail with reference to the attached drawings. Note that in the following description and drawings the same reference numerals denote the same or similar constituent elements, and, therefore, descriptions of the same or similar constituent elements are omitted.

Cell Analysis

The present disclosure relates to supporting measurement of cells in a cell analysis requested by a client. First, an outline of cell analysis will be described. Cell analysis in the present disclosure includes measurements of cells performed for research and diagnostic purposes. Cell analysis includes measuring a plurality of measurement items, which correspond to target molecules capable of detecting (preferably identifying) measurement target cells. Hence, cell analysis in the present disclosure involves detecting multiple target molecules. The target molecule is not limited insofar as the molecule is present in cells. The target molecule may be present on the cell membrane, in the cell membrane, or in the cell. The target molecule also may be an intracellular organelle (nucleus, nuclear membrane, nucleoli, mitochondria, endoplasmic reticulum, Golgi apparatus, lysosome, cell membrane, cytoplasm, and the like). The target molecule also may be, for example, a molecule obtained by gene transfer or the like. The target molecule is preferably at least one selected from a group consisting of an antigen and a nucleic acid.

A plurality of measurement items (target molecules) are intended for a plurality of measurement items (target molecules). A plurality of target molecules are the same or different biomolecules (ions (hydrogen ions, calcium ions, magnesium ions, sodium ions, potassium ions, chloride ions, zinc ions, copper ions, iron ions, and the like), proteins, sugar chains and the like, lipids, glycoproteins, glycolipids, lipoproteins, nucleic acids and the like), and are preferably different biomolecules.

The target molecule can be detected by a known method according to its physical properties. The detection can be performed, for example, by receiving the fluorescence signal of the fluorescent stain given off from the target molecule by a predetermined detector. Here, the fluorescent stain itself includes a substance that emits a fluorescence signal when irradiated with excitation light, and although the stain itself does not emit a fluorescence signal, includes a stain that converts to a material that emits a fluorescence signal in the intracellular environment after being taken into the cell.

For example, when the target molecule is a protein, a sugar chain, a lipid, a glycoprotein, a glycolipid, a lipoprotein or the like, the fluorescent stain can be bound to the target molecule by an immunological method. A fluorescent antibody method is preferred as an immunological method. When the target molecule is a sugar chain, a glycoprotein, a glycolipid or the like, the fluorescent stain can be bound to the target molecule by a method utilizing lectin activity. As a method utilizing lectin activity, preferably, a fluorescent lectin method using a fluorescently labeled lectin is used. When the target molecule is a nucleic acid, the fluorescent stain can be bound to the target nucleic acid by a hybridization method, a PCR method, a labeling method using a labeled nucleotide or the like. As a detection method of a target nucleic acid, preferred are fluorescence in situ hybridization method and fluorescence end labeling method (including a TUNEL method). When the target molecule is a lipid, glycolipid or the like, a fluorescent stain such as Nile Red can be bound to the target molecule.

Examples of a fluorescent stain to be bound to the antibody or nucleic acid, include fluorescein derivative, rhodamine derivative, Texas Red, Cy stain, Alexa (registered trademark) Fluor, MegaStokes (trademark) Dye, Oyster (trademark), DyLight (trademark), HiLyte (trademark)) Fluor, Brilliant Violet (registered trademark), Qdot (registered trademark), phycoerythrin (PE), allophycocyanin (APC), PerCP, tetramethylrhodamine (TRITC), and tandem stains of same. More specific examples include AMCA, Pacific Blue, Alexa Fluor 405, Pacific Orange, Krome Orange, Brilliant Violet 421, Brilliant Violet 510, Brilliant Violet 605, Brilliant Violet 650, Brilliant Violet 711, Brilliant Violet 785, Alexa Fluor 488, Qdot (R) 605, FITC, PE/RD1, ECD/PE-Texas Red, PC5/SPRD/PE-Cy5, PC5.5/PE-Cy5.5, PerCP, PerCP-Cy5.5, PE-Alexa Fluor 700, PC7/PE-Cy7, PE-Alexa Fluor 750, TRITC, Cy3, Alexa Fluor 594, Texas Red, Alexa Fluor 647, Alexa Fluor 700, Cy5, Cy5.5, APC, APC7/APC-Cy7, APC Alexa Fluor700, APC Alexa Fluor750 and like.

When the target molecule is an ion, an ion probe that detects each ion can be used. The ion probe can emit a fluorescence signal. As a calcium ion probe, for example, Fura 2, Fluo 3, Indo 1, Rhod 2, Fura Red and the like can be mentioned. Examples of zinc probes include Zinquinethyl ester and Dansylaminoethyl-cyclen. BCECF which is a pH probe, SNARF-1 and the like can be mentioned as a hydrogen ion probe. As a sodium ion probe, SBFI can be mentioned. As a potassium ion probe, PBFI can be mentioned.

When the target molecule is an organelle, it can be detected by a fluorescent staining method that specifically stains the organelle. Examples of fluorescent staining methods when the intracellular organelle is a nucleus include propidium iodide (PI), ethidium bromide (EB), acridine orange (AO), 4', 6-diamidono-2-phenylindole (DAPI), Hoechst 33342, Hoechst 33258, Vybrant (trademark) DyeCycle (trademark) Violet, YOYO-1, CPO, pyronin Y (Pyronin G), 7-amino-actinomycin D (7-AAD), ethidium homodimer-1, SYTO 9 green fluorescent nucleic acid stain, SYBR green I, LDS751, DRAQ5 (trademark), DRAQ7 (trademark), TO-PRO (trademark) and the like.

Target molecules that can be obtained by gene transfer and the like include EBFP, ECFP, Keima-Red, AmCyan, EGFP, ZsGreen, EYFP, mBanana, mOrange, DsRed, tdTomato, mcherry, E2-Crimson, Keima-Red, Kusabira-Orange and the like.

The above-mentioned method is a method of directly binding a fluorescent stain to a target molecule and detecting its fluorescence signal. On the other hand, detection of a target molecule by a fluorescent stain is not limited to the above embodiment. For example, the presence of a target molecule can be detected indirectly by detecting a phenomenon caused by the function of the target molecule or reflecting the function of the target molecule using a fluorescent stain. For example, when the target molecule is involved in cell proliferation, cell proliferation may be detected by CFSE or the like. When the target molecule is involved in mitochondrial membrane potential, for example, the mitochondrial membrane potential also may be detected by JC-1, Rhodamine-123 and the like. When the target molecule is involved in intracellular redox reaction, for example, intracellular thiol activity may be detected by mClB, CMFDA and the like. When the target molecule is associated with cell viability, Calcein-AM, PKH26, FDA and the like can detect cell viability. When the target molecule changes the membrane potential of the cell membrane, for example, the membrane potential of the cell membrane can be detected by DiOC2 (3), DiBAC4 (3) or the like. When the target molecule relates to the generation of reactive oxygen in cells, the generation of reactive oxygen can be detected by DCFH-DA, DHR or the like.

A reagent including an antibody to which a fluorescent stain is bound, a nucleic acid to which a fluorescent stain is bound, a staining substance that emits a fluorescence signal and the like which are used to detect the target molecule are called fluorescent reagents. A fluorescent reagent can be suitably combined with a plurality of fluorescent reagents according to a measurement item contained in an examination order. Preferably, when a target molecule is detected as an antigen, an antibody used for detection of the antigen is referred to as a detection antibody. The fluorescent reagent including a detection antibody may be a single antibody reagent comprising the detection antibody for detecting one antigen. In certain embodiments, the fluorescent reagent including a detection antibody can be a cocktail antibody reagent including a plurality of detection antibodies for detecting two or more antigens. Multiple single antibody reagents also may be combined to detect multiple target molecules. In another embodiment, one or more single antibody reagents and a cocktail antibody reagent may be combined to detect multiple target molecules. In another embodiment, multiple cocktail antibody reagents may be combined to detect multiple target molecules.

A cocktail antibody reagent is a reagent that contains a mixture of multiple types of antibodies that can bind to different or identical antigens. For example, one cocktail antibody reagent can include 2 to 6 antibodies. Here, at least one antibody of each antibody contained in one cocktail antibody reagent binds to one antigen. In an antibody contained in the cocktail antibody reagent, two or more antibodies also may be bound to one fluorescent stain. The number of antibodies contained in one cocktail antibody reagent is called the number of cocktails. Moreover, a single antibody reagent is a reagent containing one type of antibody capable of binding to an antigen.

Each fluorescent reagent has information of the target molecule to which the fluorescent reagent corresponds (name, gene ID, disease related to the target molecule, value reflecting the amount of target molecule per cell in each cell type if there is an isoform), information of the fluorescent stain (type of fluorescent stain, fluorescence intensity for each reagent manufacturer and each measuring device, the excitation light wavelength, and fluorescence wavelength), and information of the expiration date, lot number, manufacturer name, price (including running cost per assay), and dilution ratio if dilution is required. These pieces of information may be linked to the information related to the measurement item. The value reflecting the amount of target molecule is preferably the number of molecules. Hereinafter, for convenience, the "value reflecting the amount of the target molecule" may be referred to as "the number of target molecules".

The predetermined detector for receiving the fluorescence signal includes a light receiving unit capable of receiving the target fluorescence signal, and is not limited insofar as the received fluorescence signal can be delivered to a processing unit described later. For example, a cell analyzer 200 such as a fluorescence microscope, a fluorescence image scanner, or a flow cytometer is preferably used as a detector. The cell analyzer is preferably a flow cytometer.

Cell analysis also may include a pretreatment for preparing a measurement sample from a specimen. The sample is not limited insofar as it is a cell, a tissue, a fluid containing cells or the like collected from an individual. Pretreatment is a process to prepare a measurement sample (suspension liquid of cells bound to a fluorescent stain) that can be measured by the cell analysis device 200 by mixing a sample or a cell sample prepared by diluting or fixing cells derived from the sample, and a fluorescent reagent. The sample is preferably peripheral blood, bone marrow or the like. For example, in the case of multi-color flow cytometry, generally, with respect to one cell sample, all the plurality of measurement items included in the examination order are divided into one to several assays and measurement is performed for several measurement items. A set of all the measurement items included in the examination order is also called a panel. A set of several measurement items measured in one assay is also referred to as a sub-panel. For example, when a panel includes 20 measurement items, the measurement items are generally divided into 4 to 10 sub-panels, and cells are measured one sub-panel at a time.

SUMMARY OF DISCLOSURE

FIG. 1 shows an example (FIG. 1A) of the operation of a support apparatus for selecting a fluorescent reagent (hereinafter referred to as "reagent selection support apparatus") 100 used in cell analysis in the present disclosure, and one example of a screen display (FIG. 1B). When the examiner receives the examination order, the examiner sets measurement items according to the contents of the request. The reagent selection support apparatus 100 acquires the contents of the measurement item by, for example, the input by the examiner (step S1 in FIG. 1A). In the example shown in FIG. 1B, the examination order (the cell type is CD4 positive T-cells, and the measurement items satisfying the request (type of target molecule) are CD4 and CD28, which are surface antigens of T-cells. Next, the reagent selection support apparatus 100 acquires the property of the target molecule (preferably, information related to the amount of target molecule present per measurement target cell) in step S2 of FIG. 1A, and acquires the property of the fluorescent stain (preferably, information related to the type of fluorescence and its fluorescence intensity) in step S3 of FIG. 1A. In the example shown in FIG. 1B, the property of the amount of target molecule are information on how many CD4 molecules are present per CD4 positive T-cell, and how many CD28 molecules are present per CD28 positive T-cell. Moreover, in the example shown to FIG. 1B, the characteristic of a fluorescent stain is information of the fluorescence intensity of various usable fluorescent stains. In step S4 of FIG. 1A, the reagent selection support apparatus 100 outputs candidates of combinations of fluorescence formulas suitable for the examination. In the example shown in FIG. 1B, PerCP and PE are output as a combination of fluorescent reagents suitable for measuring CD4 and CD28 in the same assay.

For example, in FIG. 1B, as shown in the third column, the number of molecules of CD4 per cell (which may be represented by "number of molecules/cell") is 100,000, and the number of molecules of CD28 per cell is 20,000. That is, the number of molecules of CD28/cell is ⅕ that of CD4. In such a case, if a fluorescent stain having a fluorescence intensity higher than the fluorescence intensity for detecting CD28 is bound to CD4, the fluorescence signal derived from CD28 may not be detected when the fluorescence signal is detected.

In order to avoid such risks, in the present disclosure when different target molecules present in one measurement target cell are detected using different fluorescent stains for each target molecule in one assay, a combination of fluorescent reagents that can detect the fluorescence signal derived from any target molecule is determined. Specifically, candidates for an appropriate combination of a plurality of fluorescent stains are output based on the fluorescence intensity of each fluorescent stain and the number of molecules per cell of each target molecule. In this way, cell analysis can be performed with a combination of appropriate fluorescent reagents even in the case of an examiner inexperienced in cell analysis.

First Embodiment

Structure Summary

Figure 2:
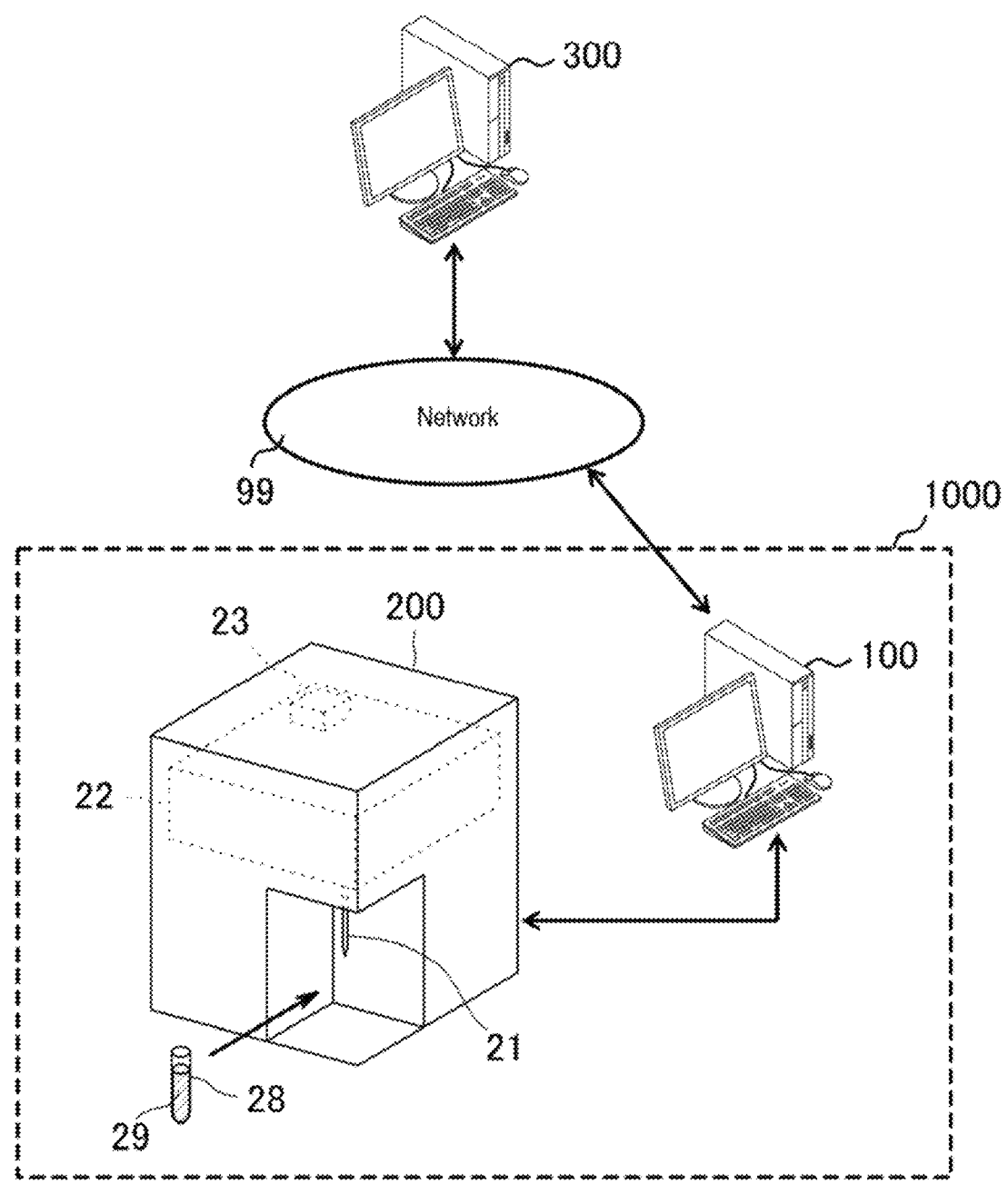
FIG. 2 is a schematic view illustrating a cell analysis system according to a first embodiment.

The first embodiment of the present disclosure relates to a reagent selection support apparatus 100. As shown in FIG. 2, the reagent selection support apparatus 100 may be connected to the cell analysis device 200 to configure a cell analysis system 1000. The reagent selection support apparatus 100 also may be connected to a requester terminal 300 through a network 99.

The reagent selection support apparatus 100 is configured by, for example, a general-purpose computer, and outputs an appropriate combination of fluorescent reagents corresponding to a plurality of measurement items based on a procedure shown in a flowchart to be described later. The examiner prepares a measurement sample 29 by mixing the cell sample with the fluorescence reagent based on the combination of the fluorescent reagents determined by the reagent selection support apparatus 100. The prepared measurement sample 29 is stored in a sample container 28, set in the cell analyzer 200, and measurement of cells is performed. Note that the reagent selection support apparatus 100 is not limited to a computer, and may be, for example, a portable terminal such as a tablet terminal.

Hardware Structure of Reagent Selection Support Apparatus

Figure 3:
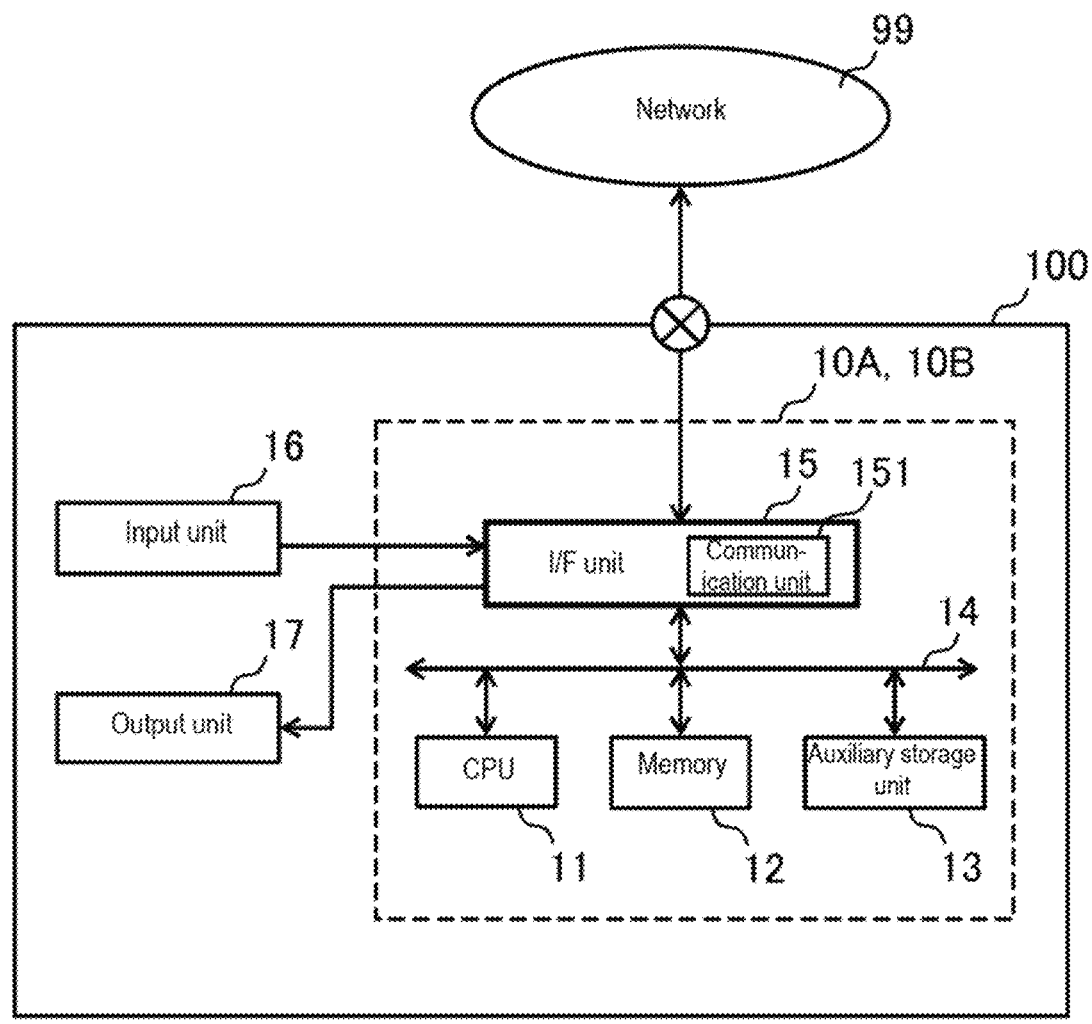
FIG. 3 is a block diagram showing a hardware structure of a support apparatus.

An example of a structure of the reagent selection assistance apparatus 100 is shown in FIG. 3. The reagent selection support apparatus 100 includes a processing unit 10A. The reagent selection support apparatus 100 also may include an input unit 16 and an output unit 17.

A processing unit 10A includes a CPU (central processing unit) 11 that performs data processing, which will be described later, a memory 12 that is used as a work area for data processing, an auxiliary storage unit 13 that stores programs and processing data that will be described later, and an interface unit 15 (hereinafter referred to as an "I/F unit") that performs data input/output and communication with an external device. An interface unit that communicates in the interface unit 15 is referred to as a communication unit 151. An input unit 16 and an output unit 17 are connected to the processing unit 10A. In the present disclosure, the memory and the auxiliary storage unit 13 may be collectively referred to as a storage unit. By way of example, the input unit 16 and the output unit 17 can be integrated and configured as a touch panel type input display device.

Figure 5:
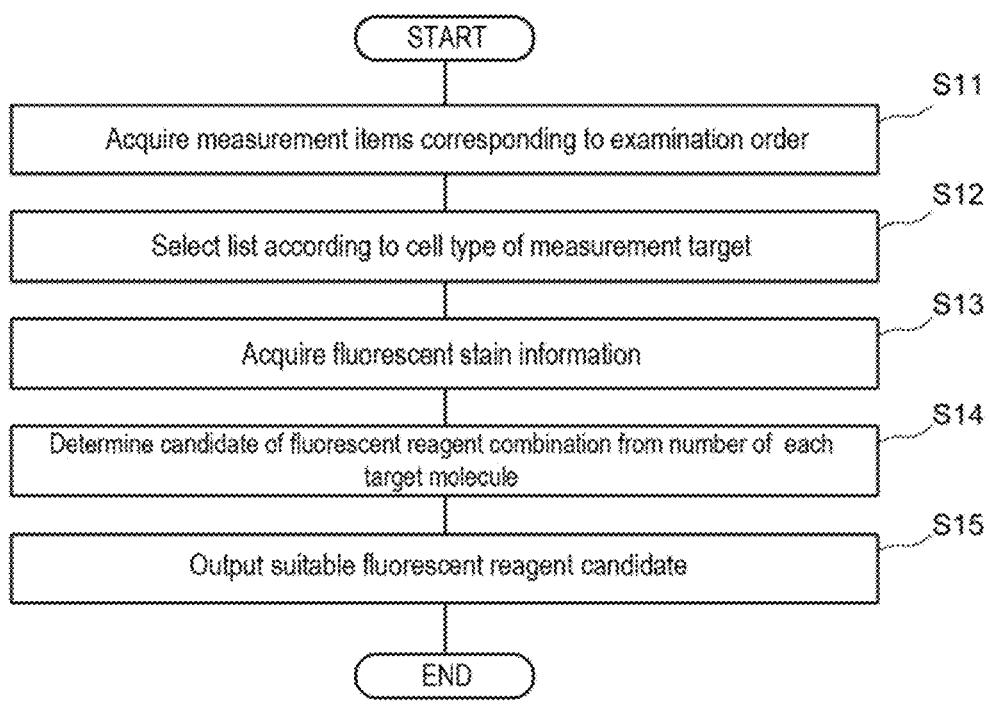
FIG. 5 is an example of a flowchart showing a procedure for determining candidates for combinations of fluorescent reagents.
Figure 9:
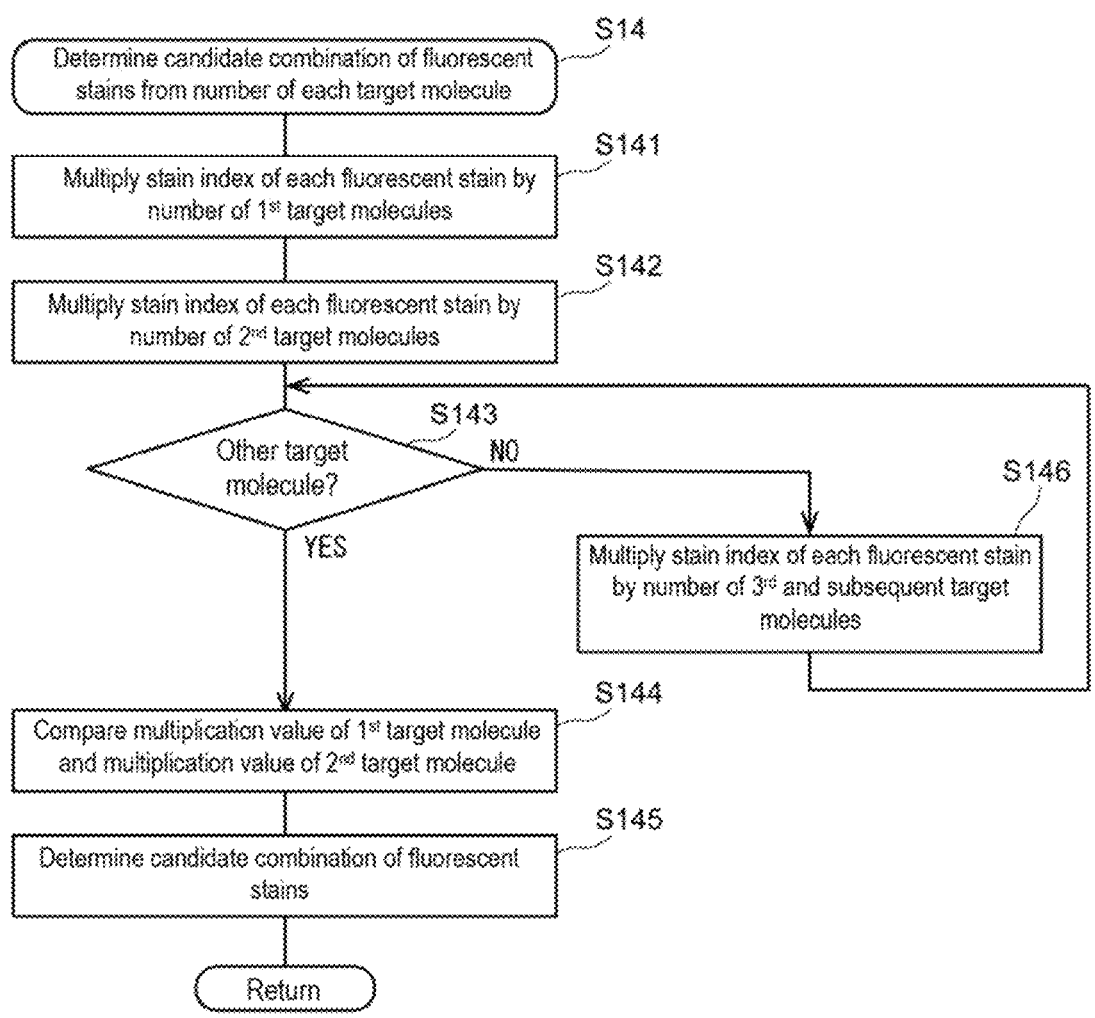
FIG. 9 is an example of a flowchart showing a procedure for determining candidates for combinations of fluorescent reagents.

The processing unit 10A performs processes using a program stored in the auxiliary storage unit 13, the program according to the present disclosure being and executable type pre-stored in the auxiliary storage unit 13 (for example, converted/generated from a programming language by a compiler) in order to perform processing of each step described in FIG. 5 and FIG. 9.

In the following description, unless otherwise specified, the processing performed by the processing unit 10A actually means the processing performed by the CPU 11 based on the program stored in the auxiliary storage unit 13 or the memory 12. The CPU 11 temporarily stores necessary data (intermediate data during processing and the like) using the memory 12 as a work area, and appropriately stores long-term storage data such as calculation results in the auxiliary storage unit 13.

Function Block of Reagent Selection Support Apparatus

Figure 4:
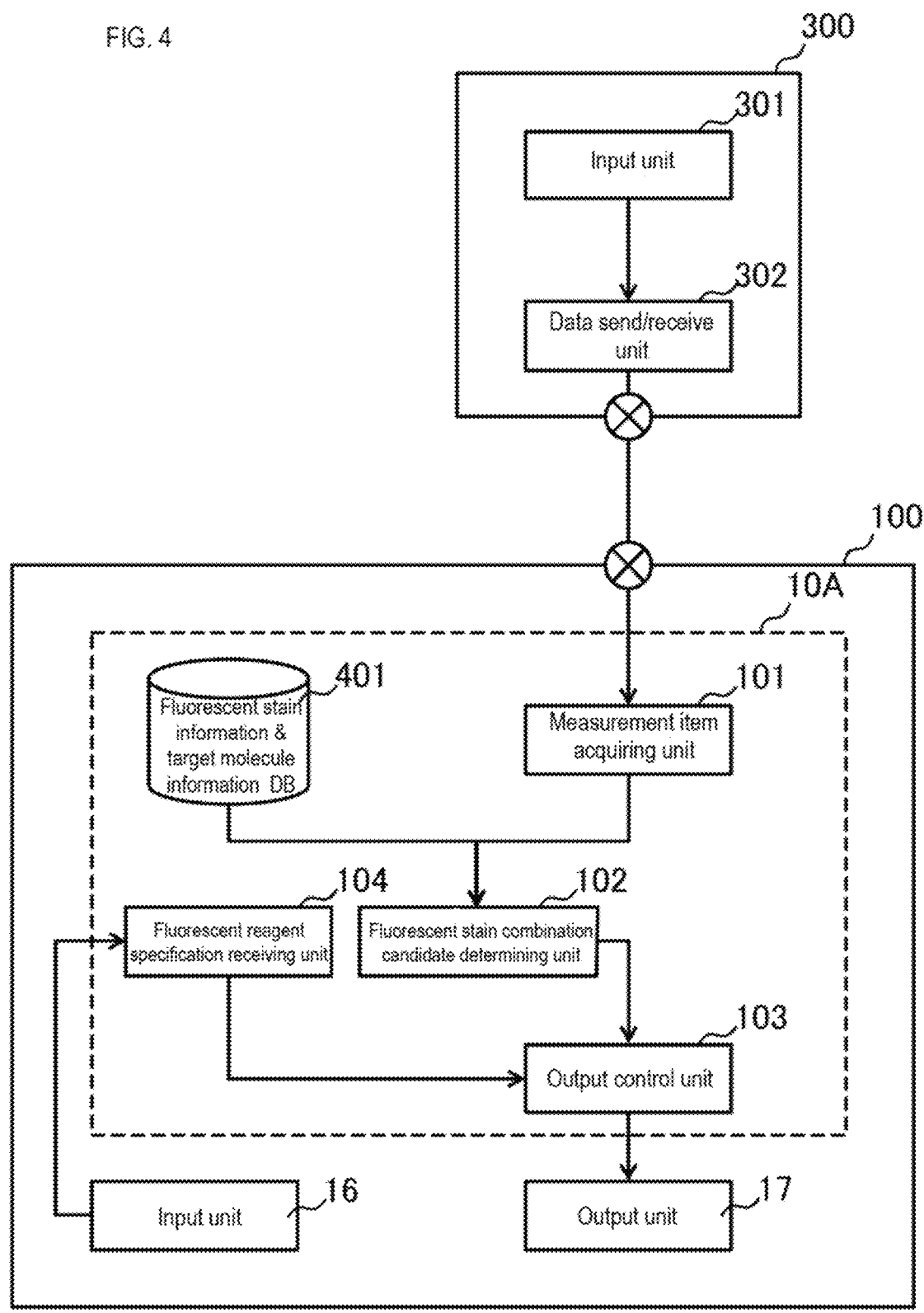
FIG. 4 is a block diagram illustrating the function of the cell analysis system according to the first embodiment.

An example of a function block of the reagent selection support Apparatus 100 is illustrated in FIG. 4. The processing unit 10A of the reagent selection support apparatus 100 includes a measurement item acquiring unit 101, a candidate fluorescent stain determining unit 102, an output controller 103, and a fluorescent reagent specification receiving unit 104. The measurement item acquiring unit 101, the output controller 103, and the fluorescent reagent specification receiving unit 104 correspond to the I/F unit 15, and the candidate fluorescent stain determining unit 102 corresponds to the CPU 11, respectively. These function blocks are realized by installing the program according to the present disclosure in the auxiliary storage unit 13 of the processing unit 10A, or temporarily storing the program in the memory 12, and executing the program by the CPU 11.

The measurement item acquiring unit 101 receives the content of the examination order from a client terminal, for example, from the input unit 16 or via the network 99. The candidate fluorescent stain determining unit 102 determines a candidate for the combination of fluorescent reagents, for example, in accordance with each step described later. The output control unit 103 outputs the determined candidate. The fluorescent reagent specification accepting unit 104 accepts selection of a combination of fluorescent reagents designated by the examiner.

In the first embodiment, the fluorescent stain information and the target molecule information database 401 (hereinafter referred to as "fluorescent stain information and target molecule information DB401") are stored in the auxiliary storage unit 13 or the memory 12 of the processing unit 10A. The fluorescent stain information and the target molecule information DB401 may be stored in advance in the auxiliary storage unit 13. The fluorescent stain information and the target molecule information described in the above "Cell Measurement" are stored in the fluorescent stain information and target molecule information DB401.

Method of Determining Candidate Combinations of Fluorescent Reagents

The following describes a method of determining a candidate combination of fluorescent reagents performed by the processing unit 10A when the examination items are CD4 positive T-cells shown in FIG. 1, the measurement items are CD4 and CD28, and the fluorescent reagent is an antibody reagent, for example.

In step S11 shown in FIG. 5, the processing unit 10A acquires information on a plurality of measurement items included in the examination order input by the examiner from the input unit 16. The information on the measurement items is, for example, the name of the target molecule. Alternatively, the processing unit 10A may acquire the examination order input by the requester from the input unit 301 of the requester terminal 300 via the network 99. The examination order is transmitted from, for example, the data send/receive unit 302 of the client terminal 300 in text format data.

The processing unit 10A selects the list from the fluorescent stain information and the target molecule information stored in the target molecule information DB401 in accordance with the cell type included in the examination order in step S12.

FIG. 6 shows an example of a list table listing information of target molecules. The information of the target molecule shown in FIG. 6 includes the type of target molecule which can detect or identify the cell type for each cell type, and the number of molecules of the target molecule per cell. Here, for example, CD28 expressed on CD4 positive T-cells and CD8 positive cells differs in the number of molecules/cell depending on the T-cell subtype. In addition, CCR5 has two isoforms with different molecular weights in one cell. Therefore, information on the target molecule is stored for each cell type, and the number of molecules of each isoform/cell when there is an isoform.

In step S13, the processing unit 10A acquires information on the fluorescent stain from the fluorescent stain information and the target molecule information DB401.

FIG. 7 shows an example of a list table in which information of fluorescent stains is listed. FIG. 7A shows the type of each fluorescent stain and the average staining index of each fluorescent stain determined using company A's CD4 antibody. FIG. 7B shows the type of each fluorescent stain and the average staining index of each fluorescent stain determined using company B's CD4 antibody. The staining index is one of the values indicating the fluorescence intensity. The staining index is a normalized value that allows the fluorescence intensities of various fluorescent stains to be compared with each other in flow cytometry applications. The mean fluorescence intensity (MFI) of the negative population minus the MFI of the positive population can be determined by dividing the standard deviation (SD) of the negative population by 2 times the value.

Figure 8:
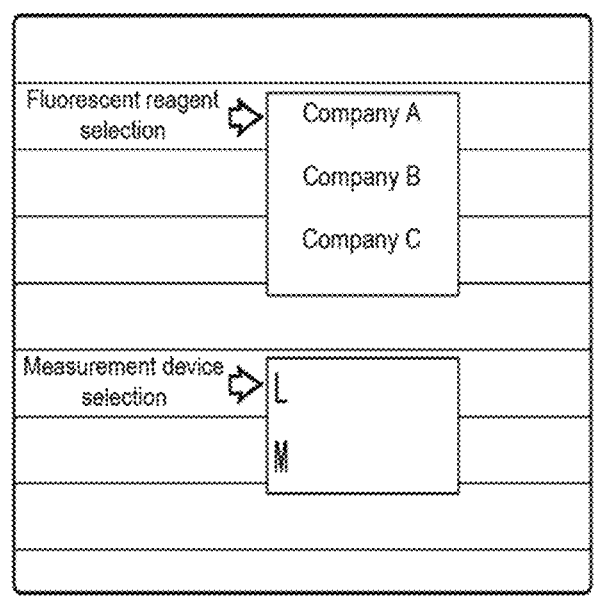
FIG. 8 is an example of a selection list of fluorescent reagents and a selection list of measurement devices.

As shown in FIG. 7, the staining index differs depending on the manufacturer of the fluorescent reagent, the measuring instrument and the like. Therefore, the processing unit 10A selects the list of information on the fluorescent stain according to the manufacturer of the fluorescent reagent used by the examiner and the measuring device. The makers of the fluorescent reagent and the measuring device may be stored in advance in the auxiliary storage unit 13. Also, the examiner may select the maker of the fluorescent reagent and the measuring device from a pull-down list as in the example of the screen shown in FIG. 8, for example, and the processing unit 10A may receive the selected information.

In step S14, the processing unit 10A determines the combination of a plurality of fluorescent reagents based on the number of molecules per cell of each target molecule based on the information related to the plurality of measurement items, that is, the information of the target molecule corresponding to each measurement item. A combination of a first fluorescent stain (a first fluorescent stain bound to a first target molecule) to be used to measure a first measurement item, and a second fluorescent stain (a second fluorescent stain bound to a second target molecule) to be used to measure a second measurement item different from the first measurement item is determined. Preferably, the combination of the plurality of fluorescent reagents is determined based on the brightness of the first fluorescent stain and the brightness of the second fluorescent stain in one cell.

A specific example of the method of determining the combination of fluorescent reagents is shown in FIG. 9. The brightness of fluorescence can be determined, for example, by multiplying the number of molecules per cell of each target molecule by the fluorescence intensity of each fluorescent stain. Here, the number of molecules per cell of each target molecule may be an absolute value or a relative value to the number of molecules of other target molecules per cell. For example, taking the CD4 positive T-cells shown in FIG. 6 as an example, the absolute value of the number of molecules of each target molecule is CD4: 100,000, CD28: 20,000, CCR5 upper stage: 4,000 and CCR5 upper stage: 24,000. Assuming that the absolute value of the number of CD28 molecules is 1, and the number of other target molecules is expressed as a relative value, CD4: 5, CD28: 1, CCR5 upper stage: 0.2 and CCR5 upper stage: 1.2. Hereinafter, each step will be described by way of example where the number of target molecules per cell is an absolute value.

In step S141 shown in FIG. 9, the processing unit 10A multiplies the number of molecules of the first target molecule shown in FIG. 6 by the staining index of each fluorescent stain shown in FIG. 7. In step S142, the processing unit 10A multiplies the number of molecules of the second target molecule shown in FIG. 6 by the staining index of each fluorescent stain shown in FIG. 7. Here, although step S141 is described first for convenience of explanation, either of steps S141 and S142 may be performed first.

If there are two target molecules to be measured, the process proceeds to "YES" in step S143, and in step S144, the processing unit 10A compares the multiplication value determined for the first target molecule with the multiplication value determined for the second target molecule.

Subsequently, in step S145, the processing unit 10A determines a different fluorescent stain having a small difference between the multiplication value determined for the first target molecule and the multiplication value determined for the second target molecule as the fluorescent stain to be bound to the first target molecule and the second target molecule. The difference is preferably the dispersion of each product value.

When a third and subsequent molecules are included in the examination order as target molecules, the process proceeds to "NO" in step S143, and in step S146, for each of the third and subsequent target molecules, the multiplication value of the number of molecules of each target molecule and the staining index of each fluorescent stain is calculated similarly to step S141 and step S142.

Subsequently, the process proceeds to "YES" when the processing unit 10A proceeds to step S143 to calculate multiplication values for all target molecules to be measured, and in step S144 the processing unit 10A compares all the calculated multiplication values for each target, and the process proceeds to step S145. When the number of target molecules is three or more, for example, the difference between the maximum value and the minimum value of each multiplication value, or a combination having a smaller dispersion of each multiplication value can be determined as a candidate.

Then, in step S15, the processing unit 10A outputs the combination candidate determined in step S14 or step 145. An example of a candidate is shown in FIG. 10. One or more candidates may be output. The candidate may be output to the storage unit as a determination result, and may be stored as a volatile value (temporarily) in memory 12, or may be stored in the auxiliary storage unit 13 in a nonvolatile manner. The candidate also may be output to the output unit 17 as a determination result. The candidate also may also be output to the communication unit 151 as a determination result and transmitted to another terminal via the network 99.

These candidate decisions may be predetermined prior to the examination. In this case, the processing unit 10A does not have to determine a plurality of candidates each time an examination is performed, which simplifies the examination.

As shown in FIG. 10, the processing unit 10A also may determine a plurality of candidates in step S145. In this case, the processing unit 10A may output the plurality of candidates directly as a determination result in step S15. Alternatively, the processing unit 10A may determine and output the most preferable candidate among the plurality of candidates. The criteria for determining the most preferable candidate among the plurality of candidates are, for example, the candidate with the smallest dispersion of brightness of the plurality of fluorescent stains, the candidate with the lowest running cost, the candidate having the shortest expiration date among the plurality of fluorescent reagents used in one assay, the candidate with a residual amount of reagent, and the candidate containing combinations of fluorescent stain and target molecule that the examiner wants to use.

For example, as shown in FIG. 10, although the first candidate has the smallest dispersion among the brightness of a plurality of fluorescent stains and the running cost is lower than that of the second candidate, there is no residual amount of reagent, and the first candidate cannot fulfill the examination order. In this case, the processing unit 10A can output the second candidate rather than the first candidate. Further, the arrangement or display of the candidates shown in FIG. 10 may be changed by rearranging according to the input of the priority from the examiner, or by not displaying combinations that cannot be used due to the residual amount of reagent or the like.

FIG. 11 shows an example of a screen displayed when the examiner inputs the priority. The examiner selects priority items such as running cost, reagent expiration date, reagent residual amount, fluorescent stain that the user wants to use and the like from a pull-down list via the input unit 16, and the processing unit 10A can output an optimum candidate from among a plurality of candidates through this input.

As described above, the process of outputting a plurality of candidates is preferable because it is possible to use the most efficient combination for examination while the examiner looks at the situation of the fluorescent reagents in the examination room at the time of measurement.

As shown in FIG. 7, the intensity of the fluorescent stain contained in the fluorescent reagent differs depending on the manufacturer of the fluorescent reagent. Therefore, in steps S141, S142 and S143 shown in FIG. 9, the product of the fluorescence intensity and the number of molecules of the target molecule is calculated for each fluorescent reagent manufacturer, and the combination of multiple fluorescent reagents to be assayed at one time may output as candidates for a preferable combination of fluorescent reagents in consideration of brightness, expiration date of fluorescent reagent, residual amount of reagent, or running cost.

Support Program

The present disclosure includes a support program that causes a computer to perform the processes of step S11 to step S15 illustrated in FIG. 5 or step S11 to step S14 illustrated in FIG. 5 and FIG. 9.

An embodiment of the present disclosure also relates to a program product, such as a storage medium, storing the support program. That is, the computer program is stored in a storage medium such as a hard disk, a semiconductor memory device such as a flash memory, or an optical disk. The storage format of the program on the storage medium is not limited insofar as the presentation device can read the program. Storage in the storage medium is preferably nonvolatile. The storage medium also may be provided as a program product.

Structure of Cell Analyzer

The cell analyzer 200 includes a suction unit 21, a fluid circuit 22, and a measurement unit 23. The cell analyzer 200 suction the measurement sample 29 contained in the sample container 28 by the suction unit 21, flows the suctioned measurement sample 29 via the fluid circuit 22, and measures the conveyed measurement sample 29 in the measurement unit 23.

In the present embodiment, control of the cell analysis device 200 is performed by the reagent selection support apparatus 100 concurrently. That is, the optical information detected by the measurement unit 23 is transmitted to the reagent selection support apparatus 100, and the reagent selection support apparatus 100 determines the number of cells and each antigen based on the optical information transmitted from the measurement unit 23. The reagent selection support apparatus 100 stores in advance in the auxiliary storage unit 13 a computer program defining a processing procedure for control of the cell analysis apparatus 200 and a processing procedure for measurement of the measurement value transmitted from the measurement unit 23 described later in the auxiliary storage unit 13 described later. The reagent selection support apparatus 100 controls the cell analysis apparatus 200 by executing a computer program by the CPU 11 described later.

The suction unit 21 is, for example, a nozzle capable of suctioning and discharging a measurement sample or the like. The fluid circuit 22 is a fluid flow path, and the fluid is transported, for example, by a syringe pump. The cell analysis system 1000 is, for example, a flow cytometer. The flow cytometer optically measures the sample by flow cytometry. By using a cocktail antibody reagent as the antibody reagent, the flow cytometer can simultaneously measure multiple types of fluorescence emitted from the sample, thus reducing the measurement time.

The number of light receiving elements (for example, photomultiplier tubes) for fluorescence detection provided in the measurement unit 23 is determined according to the number of fluorescent stains that can be handled by the cell analysis apparatus 200. For example, if the cell analysis apparatus 200 can handle 10 color fluorescent stains per assay, the cell analysis apparatus 200 includes a total of 10 light receiving elements for fluorescence detection in the measurement unit 23. Hereinafter, with reference to FIG. 12, the optical system of the flow cytometer will be described using a case of simultaneously measuring a plurality of fluorescences as an example. The dotted line represented by reference numeral 77 in FIG. 12 means that the illustration of the light receiving element which is originally present is omitted.

Figure 12:
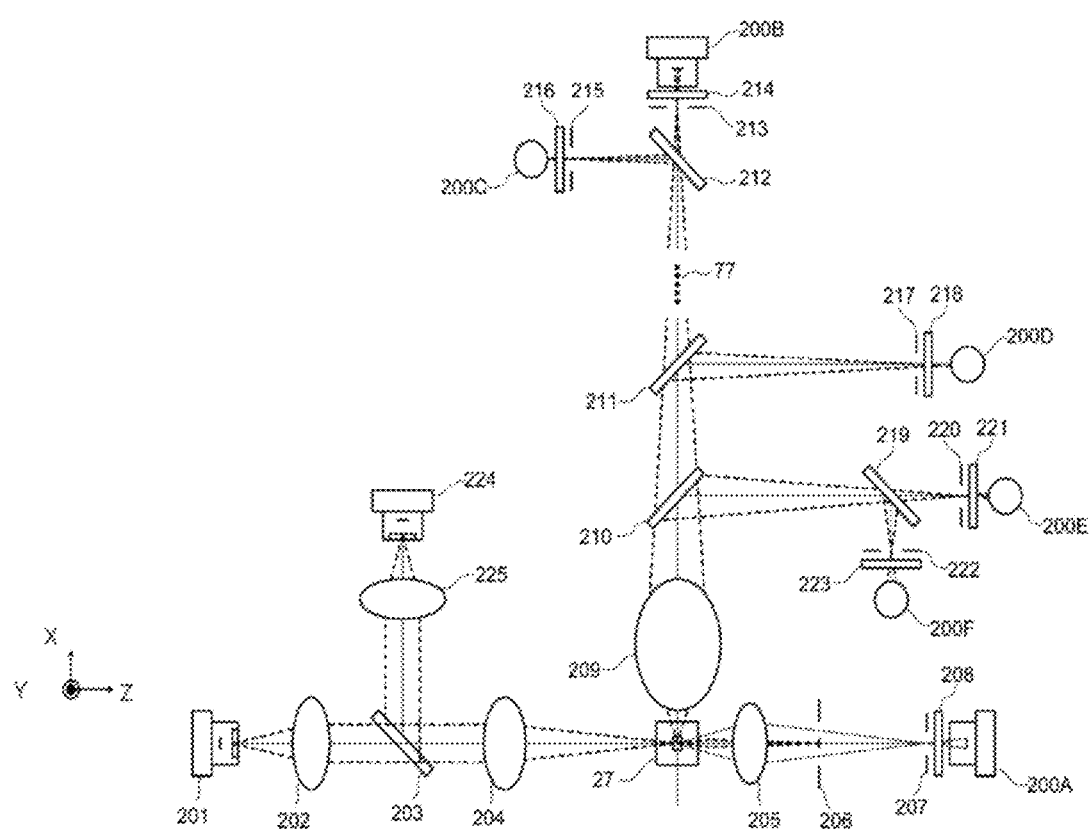
FIG. 12 is a schematic view showing an example of an optical system of a flow cytometer.

FIG. 12 illustrates an example of an optical system of a flow cytometer as an example of the measurement unit 23. The flow cytometer includes a cell 27 which receives the cell-containing liquid that contains cells in the measurement sample, light sources 201 and 224 for irradiating the cells passing through the cell 27 with light, and light receiving elements 200A to 200F for detecting optical information of the light given off by the cell and outputting a detection signal converted into an electric signal. Although the actual light sources are not just two but four, for convenience of explanation, light sources 201 and 224 will be described as an example. In the following description of the flow cytometer of FIG. 12, a case where the measurement sample 29 is a mixture of blood and an antibody reagent will be described as an example.

The cells preferably emit one or more lights when irradiated with a predetermined light. The light emitted from cells when irradiated with a predetermined light is collectively referred to as light derived from cells. The light derived from the cells includes scattered light and luminescence. The light derived from cells may be light of any wavelength, but is preferably light having a peak wavelength in the range of 400 nm to 850 nm. More specifically, the light derived from the cells is preferably fluorescent light. The light derived from the cells may be light emitted from a substance contained in the cells. Alternatively, the light derived from the cells may be detected as the light emitted from the cells as the light emitted from the fluorescent stain contained in the fluorescent reagent described in the measurement of the cells. In addition, it is preferable that light derived from cells has different peak wavelengths for each antigen. In the first embodiment, the fluorescence derived from cells is derived from the fluorescent stain labeled to each antibody contained in the fluorescent reagent.

The cell-containing liquid is a liquid containing the measurement sample drawn from the sample into the flow cytometer, and contains a dilution liquid as necessary. Optical information is information contained in one or more light wavelength spectra emitted from cells. The light wavelength spectrum includes the individual light wavelengths included in the light wavelength spectrum, the light wavelength range, and the respective light wavelengths of the light wavelength range, or the intensity of the light wavelength range. Each light wavelength and wavelength range can be specified by which one or more light receiving elements described later receive the light. The intensity of each light wavelength or light wavelength region can be specified by the received electric signal output from the light receiving element.

Hereinafter, a case where light derived from cells is scattered light and fluorescence will be specifically described as an example. The light emitted from the light source 201 passes through a collimator lens 202, a dichroic mirror 203, and a condenser lens 204 and irradiates the cell 27. The forward scattered light of the light originating from cells passing through the cell 27 is condensed, passes through a beam stopper 206, the pinhole plate 207, and the band pass filter 208, and enters the light receiving element 200A.

On the other hand, the side scattered light and the side fluorescent light derived from the cells passing through the cell 27 are collected by the collecting lens 209. The side scattered light passes through the dichroic mirrors 210, 211 and 212, the pinhole plate 203, and the band pass filter 214, and enters the light receiving element 200B. The side fluorescent light having a wavelength of 520 nm or more and 542 nm or less is transmitted through the dichroic mirrors 210 and 211, reflected by the dichroic mirror 212, passes through the pinhole plate 215 and the band pass filter 216, and enters the light receiving element 200C. The side fluorescent light having a wavelength of 570 nm or more and 620 nm or less is transmitted through the dichroic mirror 210 and reflected by the dichroic mirror 211, passes through the pinhole plate 217 and the band pass filter 218, and enters the light receiving element 200D. The side fluorescent light having a wavelength of 670 nm or more and 800 nm or less is reflected by the dichroic mirror 210, passes through the dichroic mirror 219, passes through the pinhole plate 220 and the band pass filter 221, and enters the light receiving element 200E.

The light emitted from the light source 224 passes through a collimator lens 225, a dichroic mirror 203, and a condenser lens 204 and irradiates the cell 27. The side fluorescent light derived from the cells passing through the cell 27 is collected by the collecting lens 209. The side fluorescent light of 662.5 nm or more and 687.5 nm or less is reflected by the dichroic mirror 210 and reflected by the dichroic mirror 219, and then enters the light receiving element 200F through the pinhole plate 222 and the band pass filter 223.

In the example shown in FIG. 12, a laser diode with a wavelength of 488 nm is used as the light source 201, and a laser diode with a wavelength of 642 nm is used as the light source 224. The cell 27 uses a sheath flow cell. A photodiode is used as the light receiving element 200A that receives forward scattered light, and an avalanche photodiode (APD) is used as the light receiving element 200B that receives side scattered light. Photomultiplier tubes (PMT) are used as the light receiving elements 200C to 200F that receive the side fluorescent light.

In this way, in the flow cytometer shown in FIG. 12, for convenience of explanation, the number of light receiving elements 200C to 200F that receive side fluorescent light is four. But actually there are 10 light receiving elements. Therefore, the flow cytometer shown in this example is equipped with four light receiving elements for fluorescence detection, and can simultaneously measure four colors of fluorescence per assay. However, in practice, the flow cytometer is equipped with 10 light receiving elements for fluorescence detection, and can simultaneously measure 10 colors of fluorescence per assay.

The respective detection signals output from the light receiving elements 200A to 200F are amplified in an amplifier circuit (not shown), and digitized by A/D conversion in an A/D converter (not shown). In the present embodiment, the detection signals converted into digital data are transmitted to the reagent selection support apparatus 100, and cell measurement is performed. The amplifier circuit is a known amplifier circuit configured by, for example, an operational amplifier.

The light source may be one or two or more. However, the actual flow cytometer carries four antigens. The light source is selected according to the wavelength region of light derived from cells. When the light sources are two or more, these light sources preferably emit light having different peak wavelengths.

The number of photodiodes, dichroic mirrors, and band pass filters can be varied according to the number of peak wavelengths of the light derived from cells. The types of photodiodes, dichroic mirrors, and band pass filters also can be selected according to the peak wavelength or wavelength region of the light derived from cells and the intensity thereof.

The reagent selection support apparatus 100 sends information related to detection sensitivity when the measurement unit 23 detects scattered light or fluorescent light, information related to fluorescent light correction according to the combination of the detected fluorescent reagents, and information related to gating for selecting a distribution area of the cells to be detected to the measurement unit 23, and control is performed so that the measurement unit 23 can acquire appropriate optical information according to the antigen based on the information.

Summary of Cell Analyzer Operation

In the first embodiment, information on fluorescent reagents that can be used by the cell analysis apparatus 200 (described above in the section "Measurement of cells") is stored in the reagent selection support apparatus 100. First, for example, the processing unit 10A acquires an examination order necessary for a doctor to determine whether a patient suffers from a certain disease (for example, leukemia). The reagent selection support apparatus 100 outputs a combination of a plurality of fluorescent reagents in accordance with a plurality of measurement items corresponding to the received examination order.

Thereafter, the examiner prepares the measurement sample 29 according to the combination and sets the measurement sample in the cell analysis apparatus 200. The cell analysis apparatus 200 measures each target molecule.

Requester Terminal

The cell analysis system 1000 also may be connected to a client terminal 300 via the network 99. An examination order issued by, for example, a doctor via the client terminal 300 is transmitted to the cell analysis system 1000 through the network. The requester terminal 300 is configured by, for example, a general-purpose computer having a CPU and a memory. The sample to be tested is separately delivered to the examiner. The requester terminal 300 transmits the input examination order to the reagent selection support apparatus 100. The cell analysis system 1000 also may transmit the measurement result to the client terminal 300.

The client terminal 300 includes an input unit 301 that receives an input of an examination order, and a data send/receive unit 302 that transmits an examination order to the reagent selection support apparatus 100. The client terminal 300 is a general-purpose computer, and the hardware configuration is the same as that of the reagent selection support apparatus 100 shown in FIG. 3.

Second Embodiment

In the second embodiment, the reagent selection support apparatus 100B acquires the information related to the target molecule and the information of the fluorescent dye from the external server 400. An external server 400 is configured by, for example, a general-purpose computer having a CPU, a memory, and an auxiliary storage unit.

Figure 13:
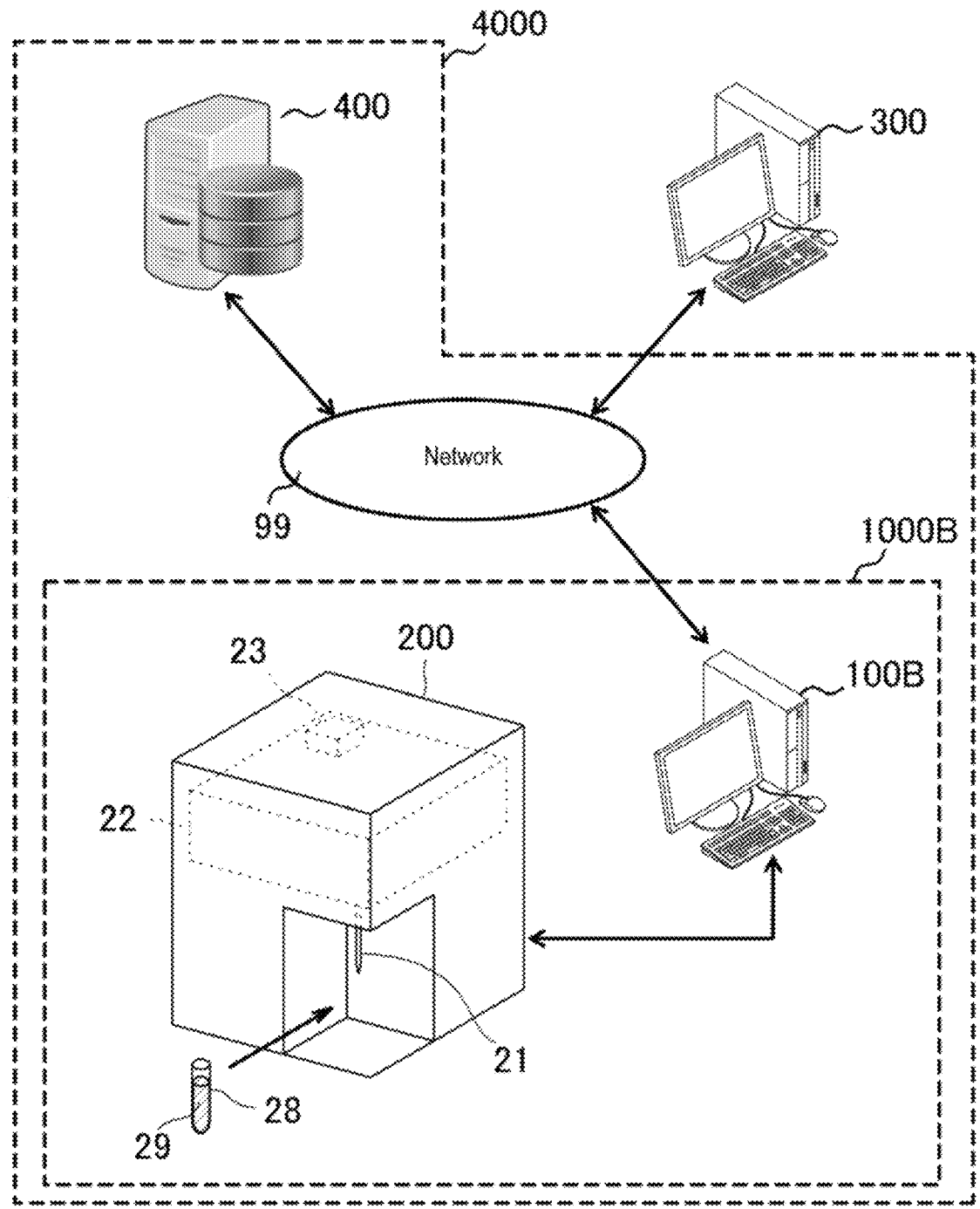
FIG. 13 is a schematic view illustrating a cell analysis system according to a second embodiment.

FIG. 13 shows an example of a cell analysis system 4000 according to the second embodiment. The cell analysis system 4000 includes a reagent selection support apparatus 100B, a cell analysis apparatus 200, and a server 400. The reagent selection support apparatus 100B and the cell analysis apparatus 200 constitute a cell analysis system 1000B. The server 400 and the cell analysis system 1000B are connected to each other through a network 99. The cell analysis system 4000 also may include a client terminal 300 connected to the cell analysis system 1000B by a network 99. The cell analysis apparatus 200 is common to the first embodiment. The hardware configuration of the reagent selection support apparatus 100B is the same as that of the reagent selection support apparatus 100.

Figure 14:
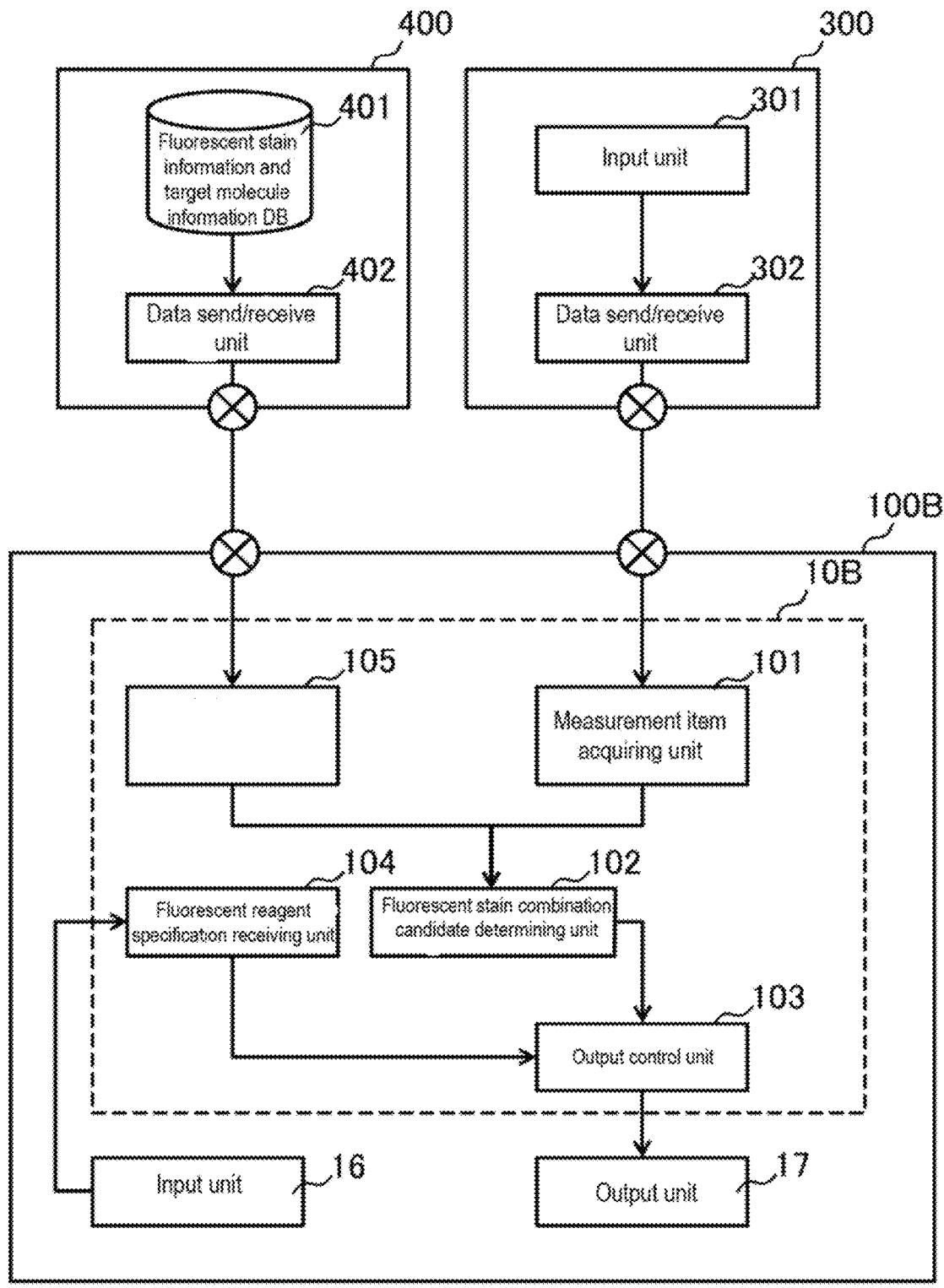
FIG. 14 is a block diagram illustrating the function of the cell analysis system according to the second embodiment.

FIG. 14 shows a function block of the reagent selection support apparatus 100B according to the second embodiment. Similar to the processing unit 10A according to the first embodiment, the processing unit 10B includes a measurement item acquiring unit 101, a candidate fluorescent dye determination unit 102, an output control unit 103, and a fluorescent reagent specification receiving unit 104. The processing unit 10B further includes a fluorescent light information and target molecule information acquiring unit 105. The measurement item acquiring unit 101, the output control unit 103, the fluorescent reagent specification receiving unit 104, the fluorescent stain information and target molecule information acquiring unit 105 correspond to the I/F unit 15, and the candidate fluorescent stain determination unit 102 corresponds to the CPU 11. These function blocks are realized by installing the program according to the present invention in the auxiliary storage unit 13 or the memory 12 of the processing unit 10B, and executing the program by the CPU 11.

The operation of the reagent selection support apparatus 100B is the same as that of the reagent selection support apparatus 100 except that the information related to the fluorescent stain and the information related to the target molecule are obtained from the server 400, hence, the description of the operation of the reagent selection support apparatus 100 is used here.

The server 400 includes a data send/receive unit 402 that transmits the fluorescent stain information and the target molecule information DB401 to the reagent selection support apparatus 100B, and a processing unit (not shown) including a CPU (not shown). The fluorescent stain information and the target molecule information DB401 are stored in the auxiliary storage unit of the server 400.

When describing using the function block shown in FIG. 14, the fluorescent stain information and target molecule information acquiring unit 105 acquires fluorescent stain information and target molecule information from the external server 400 in the second embodiment, and the acquired information is stored in the auxiliary storage 13 and memory 12 of the processing unit 10B. By updating the fluorescent stain information and target molecule information DB401 stored in the external server 400 to the latest state, the reagent selection support apparatus 100B also can constantly determine combinations of multiple fluorescent reagent based on the latest fluorescent stain information and target molecule information DB401. The method of determining the candidate of the combination of multiple fluorescent reagents is the same as in the first embodiment. The processing performed by the fluorescent stain information and target molecule information acquiring unit 105, which is a functional block, is actually performed by the processing unit 10B shown in FIG. 4.

As described above, according to the cell analysis system 4000, in addition to the effects of the cell analysis system according to the first embodiment, the fluorescent stain information and target molecule information used for measurement by the cell analysis apparatus 200 are always updated.

Updating of Fluorescent Stain Information and Target Molecule Information by Server The update of the fluorescent stain information and the target molecule information in the server 400 and the first update flow of the reagent selection support apparatus 100B will be described with reference to FIG. 15. In the first update flow, the reagent selection support apparatus 10B queries the server 400 for the presence of update information.

Figure 15:
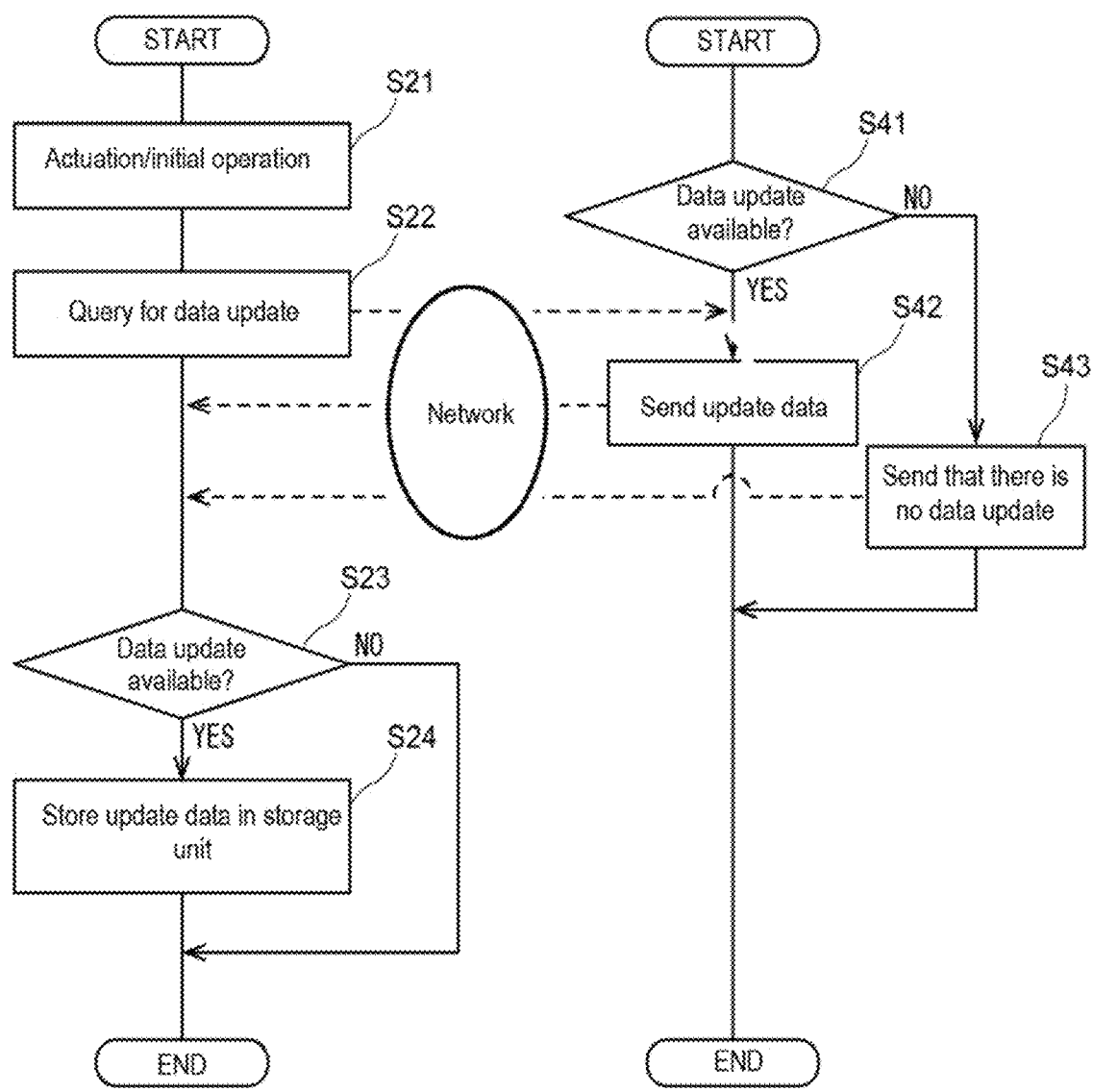
FIG. 15 is an example of a flowchart showing a procedure of updating information of a fluorescent stain and information of target molecule through a server.

In FIG. 15, when the activation and initial operation processing (step S21) of the support apparatus 100B is finished, the processing unit 10B inquires whether information of the fluorescent stain including the type of fluorescent stain, the fluorescence intensity and the like, and information of the target molecule such as target molecule type and number of target molecules per cell have been updated in the server 400 through the communication unit 151 (step S22). The CPU of the server 400 determines whether the information is updated in response to the inquiry from the reagent selection support apparatus 100B (step S41). If there is an update (YES), the CPU of the server 400 proceeds to step S42 and transmits the update data to the reagent selection support device 100B. If there is no update (NO), the process proceeds to step S43 to transmit to the reagent selection support apparatus 100B that there are no update data. The processing unit 10B determines whether there are update data (step S23). If there are update data (YES), the processing unit 10B proceeds to step S24 and stores the update data in the storage unit. If there are no update data (NO), the processing unit 10B ends the update process.

The update of the fluorescent stain information and the target molecule information in the server 400 and the second update flow of the reagent selection support apparatus 100B will be described with reference to FIG. 16. In the second update flow, when the information is updated, the server 400 accesses the reagent selection support apparatus 100B from the server 400 and transmits update data.

Figure 16:
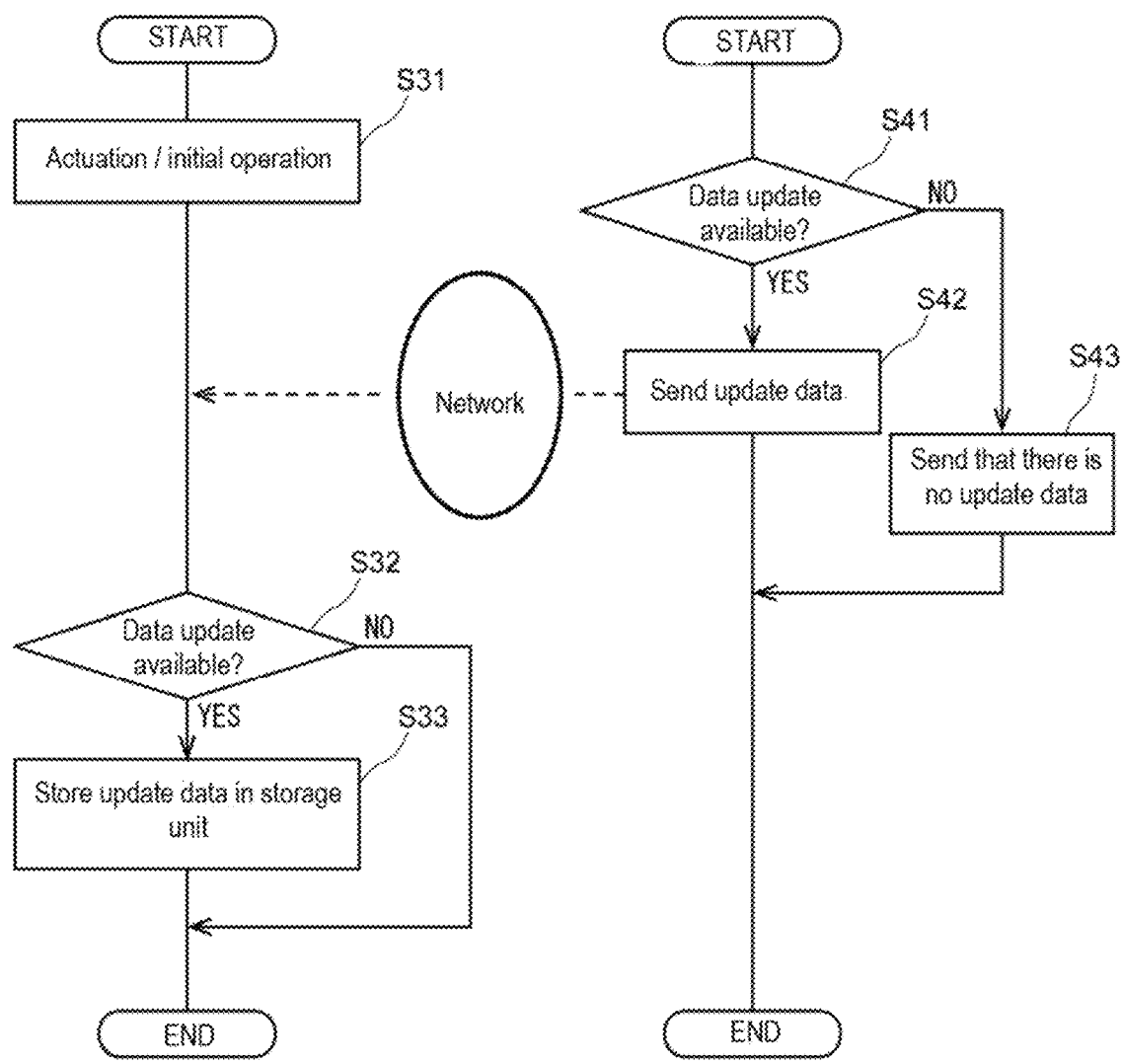
FIG. 16 is an example of a flowchart showing a procedure of updating information of a fluorescent stain and information of target molecule through a server.

In FIG. 16, the CPU of the server 400 determines whether the information of the fluorescent stain including the type of the fluorescent stain, the fluorescence intensity and the like, and the information of the target molecule such as the type of target molecule and the number of target molecules per cell are updated (step S41). If there is an update (YES), the CPU of the server 400 proceeds to step S42 and transmits the update data to the reagent selection support device 100B. If there is no update (NO), the process ends. After completion of the start-up and initial operation process (step S31), the reagent selection support apparatus 100B determines whether update data have been received from the server 400 (step S32). If there are update data (YES), the process proceeds to step S33, and the update data are stored in the storage unit. If there are no update data (NO), the update process ends.

Here, although the updated data transmitted from the server 400 may be information of the fluorescent stain including the type of the fluorescent stain and the fluorescence intensity, and information of the target molecule such as the type of target molecule and the number of target molecule per cell, the information also may be a product of the fluorescence intensity and the number of molecules per cell of the target molecule.

The reagent selection support apparatus 100B transmits the result determined as a candidate of the combination of a plurality of fluorescent reagents to the server 400 together with the information on the cell analysis apparatus 200, for example, and the server 400 stores the received information of the result and apparatus. Since the fluorescence intensity also varies depending on the measuring device, the server 400 can acquire information of the fluorescence intensity in various measuring devices and can create a database.

Other Embodiments

As mentioned above, although this invention has been described by specific embodiments, this invention is not limited to above-described embodiments.

Although the processing units 10A and 10B are realized as an integrated device in the first and second embodiments, the processing units 10A and 10B do not have to be an integrated device, and the CPU 11, the memory 12, and the auxiliary storage unit 13 and the like may be arranged separately, and connected by a network. The processing units 10A and 10B, the input unit 16, and the output unit 17 do not necessarily have to be arranged at one place, and may be arranged separately and connected so as to be communicable with each other via a network.

Although the function blocks of the measurement item acquiring unit 101, the candidate fluorescent stain determining unit 102, the output control unit 103, the fluorescent reagent specification receiving unit 104, and the fluorescent stain information and target molecule information acquiring unit 105 are executed by a single CPU 11 in the first and second embodiments, these functional blocks do not necessarily need to be executed by a single CPU 11, and may be distributed and processed by a plurality of CPUs.

Although the program for performing the process of each step described in FIG. 5 and FIG. 9 is stored in advance in the auxiliary storage unit 13 in the first and second embodiments, the program also may be installed on the processing units 10A and 10B from a CD-ROM, or computer readable non-volatile storage medium (not shown) or the like, or the processing units 10A and 10B may be connected to the network 99, and the program may be downloaded and installed from, for example, the external server 400 via the network 99.

Although the input unit 16 and the output unit 17 are integrated and realized as a touch panel type display device in the first and second embodiments, the input unit 16 also may be configured by a keyboard, a mouse or the like and output unit 17 may be configured by a liquid crystal display or the like. Alternatively, the output unit 17 may be configured by a printer or the like, and the candidate of the combination of the fluorescent reagents determined by the reagent selection support apparatus 100 may be printed.

What is claimed is:

1. A reagent selection support apparatus for supporting selection of reagents used for cell measurement, comprising:
a processor configured to acquire a measurement order including a name of a first target molecule and a name of a second target molecule other than the first target molecule, and determine, based on a first value and a second value, a combination of a first fluorescence reagent comprising a first fluorescent stain and a second fluorescence reagent comprising a second fluorescent stain, the first fluorescence reagent used to measure the first target molecule the second fluorescence reagent used to measure the second target molecule,
the first value being obtained from a value indicating an amount of the first target molecule in a cell and a value indicating an intensity of fluorescence from the first fluorescent stain, and
the second value being obtained from a value indicating an amount of the second target molecule in the cell and a value indicating an intensity of fluorescence from the second fluorescent stain; and
an output unit comprising a display, the output unit configured to output the determined combination of the first fluorescence reagent and the second fluorescence reagent.

2. The reagent selection support apparatus according to claim 1, wherein
each of the first target molecule and the second target molecule is related to an antigen containing at least one of nucleic acids, proteins, sugar chains, lipids, glycoproteins, glycolipids, lipoproteins, and ions present in the cell.

3. The reagent selection support apparatus according to claim 1, wherein
the value indicating the intensity of fluorescence from the first fluorescent stain and the value indicating the intensity of fluorescence from the second fluorescent stain are each a stain index.

4. The reagent selection support apparatus according to claim 1, further comprising:
a memory configured to store the value indicating the amount of the first target molecule in the cell, the value indicating the intensity of fluorescence from the first fluorescent stain, the value indicating the amount of the second target molecule in the cell, and the value indicating the intensity of fluorescence from the second fluorescent stain.

5. The reagent selection support apparatus according to claim 1,
wherein the processor is further configured to:
calculate information related to brightness by the first fluorescent stain based on the value indicating the amount of the first target molecule in the cell and the value indicating the intensity of fluorescence from the first fluorescent stain;
calculate information related to brightness by the second fluorescent stain the value indicating the amount of the second target molecule in the cell and the value indicating the intensity of fluorescence from the second fluorescent stain; and
determine the combination based on the information related to brightness by the first fluorescent stain and the information related to brightness by the second fluorescent stain.

6. The reagent selection support apparatus according to claim 5, wherein
the value indicating the amount of the first target molecule is a number of absolute molecules of the first target molecule or a relative number of molecules of the first target molecule present in the cell; and
the value indicating the amount of the second target molecule is a number of absolute molecules of the second target molecule or a relative number of molecules of the second target molecule present in the cell.

7. The reagent selection support apparatus according to claim 5, wherein
the processor determines the combination of the first fluorescent reagent and the second fluorescent reagent based on a dispersion of the information related to brightness of the first fluorescent stain and the information related to brightness of the second fluorescent stain.

8. The reagent selection support apparatus according to claim 1, wherein
the first fluorescent reagent includes an antibody labeled with a fluorescent stain.

9. The reagent selection support apparatus according to claim 1, wherein
the first fluorescent reagent includes an antibody for detecting one type of antigen.

10. The reagent selection support apparatus according to claim 1, wherein
the first fluorescent reagent includes a plurality of types of antibodies.

11. The reagent selection support apparatus according to claim 1, wherein
the processor determines a plurality of combinations of the first fluorescent reagent and the second fluorescent reagent, and
the output unit outputs the combination with a priority based on a remaining amount of at least one of the first fluorescent reagent or the second fluorescent reagent.

12. The reagent selection support apparatus according to claim 1, wherein
the processor determines a plurality of combinations of the first fluorescence reagent and the second fluorescence reagent, and
the output unit outputs the combination with a priority based on an expiration date of at least one of the first fluorescent reagent or the second fluorescent reagent.

13. The reagent selection support apparatus according to claim 1, wherein
the processor determines a plurality of combinations of the first fluorescent reagent and the second fluorescent reagent, and
the output unit outputs the combination with a priority based on a cost of at least one of the first fluorescent reagent or the second fluorescent reagent.

14. The reagent selection support apparatus according to claim 1, wherein
the processor determines a plurality of combinations of the first fluorescent reagent and the second fluorescent reagent, and
the output unit outputs the combination with a priority based on a setting designated by a user.

15. The reagent selection support apparatus according to claim 1, further comprising:
a communication unit comprising a network interface, the communication unit configured to receive the value indicating the intensity of fluorescence from the first fluorescent stain.

16. The reagent selection support apparatus according to claim 1, further comprising:
a communication unit comprising a network interface, the communication unit configured to receive the value indicating the amount of the first target molecule in the cell.

17. A cell analysis system comprising:
the reagent selection support apparatus according to claim 1; and
a cell analysis apparatus comprising a measurement unit having a light detector, the measurement unit to measure cells by flow cytometry using fluorescent stains determined based on the combination of the first fluorescence reagent and the second fluorescence reagent.

* * * * *

UNITED STATES PATENT AND TRADEMARK OFFICE
CERTIFICATE OF CORRECTION

| | |
|---|---|
| PATENT NO. | : 11,754,568 B2 |
| APPLICATION NO. | : 16/420443 |
| DATED | : September 12, 2023 |
| INVENTOR(S) | : Tomohiro Tsuji |

It is certified that error appears in the above-identified patent and that said Letters Patent is hereby corrected as shown below:

In the Claims

Column 21, Claim 1, Line 43, insert --and-- between "molecule" and "the".

Signed and Sealed this
Seventeenth Day of October, 2023

Katherine Kelly Vidal
*Director of the United States Patent and Trademark Office*